United States Patent
Bourke, Jr.

(10) Patent No.: US 9,682,146 B2
(45) Date of Patent: *Jun. 20, 2017

(54) METHODS AND SYSTEMS FOR TREATING CELL PROLIFERATION RELATED DISORDERS

(71) Applicant: Immunolight, LLC, Detroit, MI (US)

(72) Inventor: Frederic A. Bourke, Jr., Greenwich, CT (US)

(73) Assignee: Immunolight, LLC., Detroit, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 14/450,756

(22) Filed: Aug. 4, 2014

(65) Prior Publication Data

US 2014/0341845 A1 Nov. 20, 2014

Related U.S. Application Data

(63) Continuation of application No. 11/935,655, filed on Nov. 6, 2007, now Pat. No. 9,358,292.

(60) Provisional application No. 60/910,663, filed on Apr. 8, 2007.

(51) Int. Cl.

| | | |
|---|---|---|
| *A61K 31/37* | (2006.01) |
| *A61K 35/12* | (2015.01) |
| *A61K 31/35* | (2006.01) |
| *A61P 31/04* | (2006.01) |
| *A61P 31/12* | (2006.01) |
| *A61P 35/00* | (2006.01) |
| *A61K 41/00* | (2006.01) |
| *A61K 45/06* | (2006.01) |
| *A61K 31/714* | (2006.01) |
| *A61K 47/02* | (2006.01) |
| *A61F 7/00* | (2006.01) |
| *A61H 23/00* | (2006.01) |
| *A61K 31/366* | (2006.01) |
| *A61N 2/02* | (2006.01) |
| *A61N 5/06* | (2006.01) |
| *A61N 5/10* | (2006.01) |

(52) U.S. Cl.
CPC .......... *A61K 41/0071* (2013.01); *A61F 7/00* (2013.01); *A61H 23/00* (2013.01); *A61K 31/35* (2013.01); *A61K 31/366* (2013.01); *A61K 31/37* (2013.01); *A61K 31/714* (2013.01); *A61K 41/00* (2013.01); *A61K 41/008* (2013.01); *A61K 41/0066* (2013.01); *A61K 45/06* (2013.01); *A61K 47/02* (2013.01); *A61N 2/02* (2013.01); *A61N 5/062* (2013.01); *A61N 5/10* (2013.01); *A61N 2005/0656* (2013.01); *A61N 2005/1089* (2013.01); *A61N 2005/1098* (2013.01)

(58) Field of Classification Search
CPC ........ A61K 31/37; A61K 35/12; A61K 31/35; A61P 31/04; A61P 31/12; A61P 35/00
See application file for complete search history.

(56) References Cited

U.S. PATENT DOCUMENTS

| | | |
|---|---|---|
| 4,838,852 A | 6/1989 | Edelson |
| 4,979,935 A | 12/1990 | Lindmayer |
| 5,120,649 A | 6/1992 | Horowitz |
| 5,489,590 A | 2/1996 | Gulliya et al. |
| 5,521,289 A | 5/1996 | Hainfeld |
| 5,728,590 A | 3/1998 | Powell |
| 5,780,287 A | 7/1998 | Kraus et al. |
| 5,786,198 A | 7/1998 | Kraus et al. |
| 5,829,448 A | 11/1998 | Fisher |
| 5,952,311 A | 9/1999 | Kraus et al. |
| 5,957,960 A | 9/1999 | Chen |
| 5,980,954 A | 11/1999 | Bolton |
| 6,036,941 A | 3/2000 | Bottiroli |
| 6,042,603 A | 3/2000 | Fisher et al. |
| 6,071,944 A | 6/2000 | Rodgers |
| 6,087,141 A | 7/2000 | Margolis-Nunno |

(Continued)

FOREIGN PATENT DOCUMENTS

| | | |
|---|---|---|
| CN | 1214636 A | 4/1999 |
| CN | 1308961 A | 8/2001 |

(Continued)

OTHER PUBLICATIONS

Uyttenhove et al. European Journal of Immunology, 2004, vol. 34, No. 12, pp. 3572-3581.*

AB Santamaria et al., "p53 and Fas Ligand are Required for Psoralen and UVA-Induces Apoptosis in Mouse Epidermal Cells", Cell Death and Differentiation (200) 9, pp. 549-560, www.nature.com/cdd (12pp.).

(Continued)

*Primary Examiner* — James D Anderson
(74) *Attorney, Agent, or Firm* — Oblon, McClelland, Maier & Neustadt, L.L.P.

(57) ABSTRACT

Methods for the treatment of a cell proliferation disorder in a subject, involving:
(1) administering to the subject at least one activatable pharmaceutical agent that is capable of effecting a predetermined cellular change when activated, either alone or in combination with at least one energy modulation agent; and
(2) applying an initiation energy from an initiation energy source to the subject,
wherein the applying activates the activatable agent in situ,
thus causing the predetermined cellular change to occur, wherein the predetermined cellular change treats the cell proliferation disorder, preferably by causing an increase or decrease in rate of cell proliferation,
and a kit for performing the method, a computer implemented system for performing the method, a pharmaceutical composition useful in the method and a method for causing an autovaccine effect in a subject using the method.

13 Claims, 4 Drawing Sheets

(56) References Cited

U.S. PATENT DOCUMENTS

| | | | |
|---|---|---|---|
| 6,121,425 A | 9/2000 | Hainfeld | |
| 6,160,024 A | 12/2000 | Kraus et al. | |
| 6,204,058 B1 | 3/2001 | Bolton | |
| 6,225,333 B1 | 5/2001 | Rodrers | |
| 6,235,808 B1 | 5/2001 | Crivello | |
| 6,569,467 B1 | 5/2003 | Bolton | |
| 6,669,965 B2 | 12/2003 | Bolton | |
| 6,670,113 B2 | 12/2003 | Hainfeld | |
| 6,719,778 B1 | 4/2004 | Van Tassel et al. | |
| 6,849,058 B1 | 2/2005 | Levy | |
| 6,955,639 B2 | 10/2005 | Hainfeld | |
| 7,008,559 B2 | 3/2006 | Chen | |
| 7,045,124 B1 | 5/2006 | Hamet | |
| 7,183,072 B1 | 2/2007 | Hainfeld | |
| 7,364,872 B1 | 4/2008 | Hainfeld | |
| 7,367,934 B2 | 5/2008 | Hainfeld | |
| 8,770,203 B2 * | 7/2014 | Bourke, Jr. | A61K 41/008 128/898 |
| 9,283,275 B2 * | 3/2016 | Vo-Dinh | A61K 41/0028 |
| 9,358,292 B2 * | 6/2016 | Bourke, Jr. | A61K 41/00 |
| 9,498,643 B2 * | 11/2016 | Bourke, Jr. | A23L 3/26 |
| 2002/0127224 A1 | 9/2002 | Chen | |
| 2003/0022170 A1 | 1/2003 | Khodadoust | |
| 2004/0157767 A1 | 8/2004 | Faulk | |
| 2004/0166553 A1 | 8/2004 | Nguyen et al. | |
| 2005/0020869 A1 | 1/2005 | Hainfeld | |
| 2005/0043233 A1 | 2/2005 | Stefanic et al. | |
| 2005/0058713 A1 | 3/2005 | Russell et al. | |
| 2005/0154049 A1 | 7/2005 | Dees et al. | |
| 2006/0019876 A1 | 1/2006 | Faulk | |
| 2006/0067889 A1 | 3/2006 | Pallenberg | |
| 2006/0067941 A1 | 3/2006 | Buzatu et al. | |
| 2006/0134031 A1 | 6/2006 | Decola et al. | |
| 2006/0255292 A1 | 11/2006 | Ja | |
| 2007/0059316 A1 | 3/2007 | Pallenberg | |
| 2007/0063154 A1 | 3/2007 | Chen | |
| 2007/0217996 A1 | 9/2007 | Levy et al. | |
| 2007/0218049 A1 | 9/2007 | Chen | |
| 2007/0243137 A1 | 10/2007 | Hainfeld | |
| 2007/0274909 A1 | 11/2007 | Justel et al. | |
| 2007/0292353 A1 | 12/2007 | Levy et al. | |
| 2008/0003183 A1 | 1/2008 | Guo | |
| 2008/0031960 A1 | 2/2008 | Wilson et al. | |
| 2008/0050448 A1 | 2/2008 | Wilson et al. | |
| 2008/0089836 A1 | 4/2008 | Hainfeld | |
| 2008/0139993 A1 | 6/2008 | Bensaoula et al. | |
| 2008/0248001 A1 | 10/2008 | Bourke | |
| 2009/0104212 A1 | 4/2009 | Bourke | |
| 2009/0294692 A1 | 12/2009 | Bourke, Jr. et al. | |
| 2010/0016783 A1 | 1/2010 | Bourke, Jr. et al. | |
| 2012/0039825 A1 | 2/2012 | Decola et al. | |
| 2013/0102054 A1 | 4/2013 | Bourke, Jr. | |
| 2013/0156905 A1 | 6/2013 | Bourke, Jr. et al. | |
| 2013/0240758 A1 | 9/2013 | Bourke, Jr. et al. | |
| 2014/0134307 A1 | 5/2014 | Bourke, Jr. | |
| 2014/0163303 A1 | 6/2014 | Bourke, Jr. et al. | |

FOREIGN PATENT DOCUMENTS

| | | |
|---|---|---|
| EP | 2 150 549 | 2/2010 |
| JP | 4-501717 | 3/1992 |
| JP | 09038503 | 2/1997 |
| JP | 09299937 | 11/1997 |
| JP | 2000-511929 | 9/2000 |
| JP | 2003-528143 | 9/2003 |
| JP | 2006-524634 | 11/2006 |
| WO | WO 98/18399 A1 | 5/1998 |
| WO | WO 02/094271 A1 | 11/2002 |
| WO | WO 03/037297 A2 | 5/2003 |
| WO | WO 03/037297 A3 | 5/2003 |
| WO | 03/049801 | 6/2003 |
| WO | WO 03/057238 A1 | 7/2003 |
| WO | 05/030254 | 4/2005 |
| WO | WO 2005/120590 A1 | 12/2005 |
| WO | WO 2006/111971 A2 | 10/2006 |
| WO | 2007/048635 | 5/2007 |
| WO | 2007/108512 | 9/2007 |
| WO | WO 2008/015453 A1 | 2/2008 |
| WO | WO 2008/124681 A2 | 10/2008 |
| WO | WO 2009/114567 A1 | 9/2009 |
| WO | WO 2009/124189 A1 | 10/2009 |

OTHER PUBLICATIONS

Pathak MA., "Mechanism of psoralen photosensitization reactions", Natl Cancer Insti. Monogr, Dec. 1984: 66:41-6, Abstract, downloaded from http://www.ncbi.nlm.nih.gov/pubmed/6531038 on May 22, 2008, (1pp.).

Stanley G. Rockson, et al., "Photoangioplasty: An Emerging Clinical Cardiovascular Role for Photodynamic Therapy", Journal of the American Heart Association, Circulation 2000; 102; pp. 591-596, downloade form http://cir.ahajournals.org/cgi/content/full/102/5/591 on Mar. 26, 2008,(7pp.).

York N. Hslang et al., "Determining Light Dose for Photodynamic Therapy of Atherosclerotic Lesions in the Yucatan Miniswine", J. Endovasc Surg, 1995, 2, pp. 365-371, (7pp.).

H. Wang et al., "High-speed Mapping of Synaptic Connectivity Using Photostimulation in Channelrhodopsin-2 Transgenic mice", PNAS, May 8, 2007, vol. 104, No. 19, pp. 8143-8148, www.pnas.org/cgi/doi/10.1073/pnas.0700384104 (6pp.).

Edward M. Callaway, et al., "Photostimulation Using Caged Glutamate Reveals Functional Circuitry in Living Brain Slices", Proc. Natl. Acad. Sci. USA., vol. 90, Aug. 193, pp. 7661-7665, (5pp.).

Chilean Substantive Report issued Aug. 5, 2014 in Patent Application No. 997-2008 (with English Translation of Category of Cited Documents).

Notice of final Rejection issued Feb. 3, 2015 in Korean Patent Application No. 10-2009-7023302 (with English translation).

Office Action issued Jun. 17, 2014 in Saudi Arabian Patent Application No. 8290205 (submitting English language translation only).

Extended European Search Report issued Jul. 31, 2014 in Patent Application No. 08733147.6.

Communication pursuant to Rules 70(2) and 70a(2) EPC issued Aug. 20, 2014 in European Patent Application No. 08733147.6.

Anna C. S. Samia, et al., "Quantum Dot-based Energy Transfer: Perspectives and Potential for Applications in Photodynamic Therapy", Photochemistry and Photobiology, vol. 82, No. 3, American Society for Photobiology, XP002475785, (May 1, 2006), pp. 617-625.

Peng Zhang, et al., "Versatile Photosensitizers for Photodynamic Therapy at Infrared Excitation", Journal of the American Chemical Society, vol. 129, No. 15, XP055129527, (Mar. 27, 2007), pp. 4526-4527.

Artur Bednarkiewicz, et al., "The susceptibility of bacteria to photodynamic inactivation with lanthanide complexes of chlorin e6", SPIE-OSA, vol. 5863, XP040207472, (Jan. 1, 2005), pp. 58630V-1 to 58630-6.

Wensha Yang, et al., "Novel FRET-Based Radiosensitization Using Quantum Dot-Photosensitizer Conjugates", Conference Record of the Forty-First Asilomar Conference on Signals, Systems & Computers, (Nov. 4-7, 2007), XP031242401, pp. 1861-1865.

Office Action issued Dec. 9, 2014 in Taiwanese Patent Application No. 097111906 (with English translation).

Combined Office Action and Search Report issued Dec. 25, 2015 in Chinese Patent Application No. 201410224724.4 (with English language translation).

Office Action issued Oct. 15, 2015 in Canadian Patent Application No. 2,682,686.

Examiner's Office Action issued Mar. 13, 2015 in Canadian Patent Application No. 2,682,686.

European Office Action issued Jul. 7, 2015 in Patent Application No. 08 733 147.6.

Office Action issued Oct. 2, 2015 in Korean Patent Application No. 10-2014-7032340 (with English language translation).

English translation of the First Examination Report issued Aug. 30, 2014, in Indian Patent Application No. 7137/DELNP/2009.

(56) References Cited

OTHER PUBLICATIONS

Office Action issued Jan. 20, 2015 in Saudi Arabian Patent Application No. 113340787.
Office Action issued Oct. 15, 2015 in Australian Patent Application No. 2013231221.
Australian Office Action issued Aug. 3, 2015 in Patent Application No. 2013231221.
Office Action issued Sep. 18, 2014, in Korean Patent Application No. 10-2009-7023302 with English translation.
Office Action issued Jul. 25, 2014 in Canadian Patent Application No. 2,682,686.
Office Action issued Jul. 27, 2016, in Chilean patent application No. 2015-000382.
Office Action issued Jul. 27, 2016, in Chilean patent application No. 2015-000383.
AB Santamaria et al, "p53 and Fas ligand are required for psoralen and UVA-induced apoptosis in mouse epidermal cells", Cell Death and Differentiation (2002) 9, pp. 549-560 www.nature.com/cdd (12 pp).
Cancer vaccine therapy—autologous tissue derived tumor vaccine—treatment . . . at http://www.saisei-mirai.or.jp/gan/cvt_eng. html accessed Sep. 20, 2016 3 pp.
Vaccine-style treatment for rheumatoid arthritis retrains the immune system at http://newatlas.com/early-clilnical-trial-success-rheumatoid-arthritis-treatme . . . Accessed Sep. 20, 2016 3 pp.
Immunotherapy: Using the Immune System to Treat Cancer at https://www.cancer.gov/research/areas/treatment/immunotherapy-using-im . . . Accessed Sep. 20, 2016 3 pp.
French et al, "Identification of Clonal T Cells in the Blood of Patients With Systemic Sclerosis", *Arch Dermatol*, (2001) vol. 137, pp. 1309-1313.
Thai Office Action issued Oct. 25, 2016 in Patent Application No. 0801001775.
Combined Chinese Office Action and Search Report issued Jun. 27, 2016 in Patent Application No. 201410224724.4 (with English language translation).
Third Office Action issued Dec. 29, 2016, in Chinese patent application No. 201410224724.4 (w/ English translation).
Xiaodong Wang, "The Expanding Role of Mitochondria in Apoptosis", Genes & Development, 15, 2001, pp. 2922-2933, www.genesdev.org (12 pp.).
Reproductive and Cardiovascular Disease Research Group, downloaded from http://www.squl.ac.uk/depts/immunology/~dash/apoptosis/mito.htm on May 22, 2008, (4pp.).
Noah Scheinfeld, et al., "A Review of Studies that Have Utilized Different Combinations of Psoralen and Ultraviolet B Phototherapy and Ultraviolet A Phototherapy", Dermatology Online Journal, vol. 9, No. 5., downloaded from http://dermatology.cdlib.org/95/reviews/uv/scheinfeld.html on May 22, 2008, (8pp.).
Karen S. McGinnis, et al., "An effective and Synergistic Combined Adjunct to Therapy for Patients with Advances Cutaneous T-Cell Lymphoma", Psoralen Plus Long-Wave UV-A (PUVA) and Bexarotene Therapy, Arch Dermatol., /vol. 139, 2003, pp. 771-775,downloaded from www.archdermatol.com on May 22, 2008, (5pp.).
Pathak MA., "Mechanism of psoralen photosensitization reactions", Natl Cancer Inst. Monogr, Dec. 1984: 66:41-6, Abstract, downloaded from http://www.ncbi.nlm.nih.gov/pubmed/6531038 on May 22, 2008, (1pp.).
Stanley G. Rockson, et al., "Photoangioplasty: An Emerging Clinical Cardiovascular Role for Photodynamic Therapy", Journal of the American Heart Association, Circulation 2000; 102; pp. 591-596, downloade form http://cir.ahajournals.org/cgi/content/full/102/5/591 on Mar. 26, 2008.(7pp.).
York N. Hsiang et al., "Determining Light Dose for Photodynamic Therapy of Atherosclerotic Lesions in the Yucatan Miniswine", J. Endovasc Surg, 1995, 2, pp. 365-371. (7pp.).
Margaret T. T. Wong-Riley et al., "Photobiomodulation Directly Benefits Primary Neurons Functionally Inactivated by Toxins", The Journal of Biological Chemistry, 2005, vol. 280, No. 6, Issue of Feb. 11. pp. 4761-47771, downloaded form www.jbc.org on Mar. 27, 2008, (11pp.).
Harry Whelan, et al., "Harnessing the Cell's Own Ability to Repair and Prevent Neurodegenerative Disease", Spie, Newsroom, 10.1117/2.1200802.1014, 2008, (3pp.).
Feng Zhang et al., "Channelrhodopsin-2 and Optical Control of Excitable Cells", Nature Methods, vol. 3, No. 10, Oct. 2006, pp. 785-792, http://www.nature.com/naturemethods (8pp.).
H. Wang el al., "High-speed Mapping of Synaptic Connectivity Using Photostimulation in Channelrhodopsin-2 Transgenic mice", PNAS, May 8, 2007, vol. 104, No. 19, pp. 8143-8148, www.pnas.org/cgi/doi/10.1073/pnas.0700384104 (6pp.).
John G. McCarron, et al "Origin and Mechanisms of $Ca^{2+}$ Waves in Smooth Muscle as Revealed by Localized Photolysis of Caged Inositol 1,4,5,-Trisphosphate", The Journal of Biological Chemistry, vol. 279, No. 9, issue of Feb. 27, pp. 8417-8427, downloaded from http://www.jbc.org on Mar. 5, 2008, (1pp.).
S D Zakharov et al, "Light-Oxygen Effect in Cells and Its Potential Applications in Tumour Therapy(review)", Quantum Electronics 29 (12), 1999, pp. 1031-1053, (23pp.).
Daniel Huber et al., "Sparse Optical Microstimulation in Barrel Cortex Drives Learned Behaviour in Freely Moving Mice", vol. 451, Jan. 3, 2008, doi:10.1038, Nature 06445, Letters (6pp.).
Christopher D. Harvey et al., "Locally Dynamic Synaptic Learning Rules in Pyramidal Neuron Dendrites", vol. 450, 20/27 Dec. 2007, doi:10.1038. Nature 06416, Articles, (8pp.).
Antoine R. Adamantidis et al., "Neural Substrates of Awakening Probed with Optogenec Controll of Hypocretin Neurons", vol. 450, Nov. 15, 2007, doi: 10.1038, Nature 06310, Letters, (6pp.).
N. I. Smith et al., "Photostimulation of Two Types of $Ca^{2+}$ Waves in Rat Pheochoromocytoma PC12 Cells by Ultrashort Pulsed Nearinfrated Laser Irradiation", Letters, Wilwy-VCH Verlag GmbH & Co. DGaA, Published Oct. 13, 2005, (8pp.).
Susana W. Lima et al., "Remote Control of Behavior Through Genetically Targeted Photostimulation of Neurons", Resource Department of Cell Biology, Yale University School of Medicine, Cell, vol. 121, Apr. 8, 2005, pp. 141-152, (12pp.).
Matthias Eder et al., "Shining Light on Neurons—Elucidation of Neuronal Functions by Photostimulation", Clinical Neuropharmacology, Max-Planck-Institute of Psychiatry, Munich, Germany, Reviews in the Neurosciences, 15, 2004, pp. 167-183, (16pp.).
Katleen Braet et al., "Photoliberating Inositol-1,4,5-Trisphosphate Triggers ATP Release That is Blocked by the Connexin Mimetic Peptide Gap 26", Churchill Livingstone, Cell Calcium 33, 2003. pp. 37-48, (12pp.).
Karel Svoboda, "New Studies Illuminate the Computational Power of Neurons", HHMI, Research News, Dec. 20, 2007, (3pp.).
Photobiomodulation, Wikipedia, downloaded from http://en.wikipedia.org/wiki/Laser_therapy on Mar. 26, 2008, (2pp.).
Science News, "Pulsing Light Silences Overactive Neurons", ScienceDaily, Mar. 28, 2007, downloaded from http://sciencedaily.com/releases/2007/03/070327161418.htm on Mar. 26, 2008, (2pp.).
Science News, Scientist Directly Control Brain Cell Activity With Light, ScienceDaily, Apr. 5, 2007, downloaded from http://www.sciencedaily.com/releases/2007/04/070704162400.htm on Mar. 26, 2008 , (2pp.).
ScienceDaily, Optical Technique Studies Brain Activity without Surgery on Skull, Aug. 2, 2001 Champaign, Ill, downloaded from http://www.sciencedaily.com/releases/2001/08/010802081211.htm on Mar. 26, 2008 , (2pp.).
Jay Motola, "Enlarged Prostate Treatment: Green Light PVP", ProstateCommons.com, Monday, Nov. 5, 2007, downloaded from http://healthcentral.com/prostate/c/95/15917/gree-light-pvp/ on Mar. 26, 2008, (2pp.).
Judy Foreman, "What is 'Green Light' Laser Therapy to Treat an enlarged Prostate?", The Boston Globe, Health Answers, Sep. 3, 2007, downloaded form http://boston.com/news/golbe/health_science/articles/2007/09/03/what_is_green_light , Mar. 26, 2008, (2pp.)

(56) References Cited

OTHER PUBLICATIONS

Prof. Tiina Karu's, "Cellular Mechanism of Low-Power Laser Therapy", Photobiomodulation, downloaded from www.tinnitus.us/tiinakarupresentaion.html on Mar. 26, 2008, (6pp.).
Pascal Carmody Medical Director, "Photodynamic Therapy", The Photodynamic Treatment Center at East Clinic, Killaloe, Co. Clare, Ireland, http://www.famma.ru/technical/articles-1/photodynamic_therapy.htm downloaded on Mar. 26, 2008, (4pp.).
William E. Grant, et al., "Photodynamic Therapy of Arteries: Preservation of Mechanical Integrity", Photodynamic Therapy of Arteries: Preservation of Mechanical Integrity, http://www.lumacare.com/paper6.htm downloaded on Mar. 26, 2008, (6pp.).
S D Zakharov et al., Light-Oxygen Effect in Cells and its Potential Applications in Tumor Therapy (review), Quantum electron 29, pp. 1031-1053, 1999, Abstract, http://www.iop.org/EJ/abstract/1063-7818/29/12/r03 , downloaded on Mar. 26, 2008,(1pp.).
Zhang F. et al., "Multimodal Fast Optical Interrogation", Comment in Nature Apr. 5, 2007; 446 (7136):617-9, Abstract, (1pp.).
Marleny Elizabeth Marquez Martinez et al., "Effect of IR Laser Photobiomodulation on the Repair of Bone Defect Grafted with Organic Bovine Bone", Journal Lasers in Medical Science, Springerlink Dae, Thursday, Sep. 20, 2007, Abstract, (2pp.).
Yasuyuki Nemota et al., "Inductive and Inhibitory Effects of Light on Cell Division in Chattonella Antigua", Plant and Cell Physiology, Oxford Journals, vol. 26, No. 4, pp. 669-674, Abstract, downloaded from http://pcp.oxfordjournals.org/cgi/conlent/abstract/26/4/669 on Mar. 26, 2008, (1pp.).
Arany PR. et al., "Activation of Latent TGf-beta1 by Low-Power Laser in Vitro Correlates with increased TGF-beta 1 Levels in Laser-enhanced Oral Wound Healing", Wound Repair Regen, Nov.-Dec. 2007;15(6):866-74, Abstract, (1pp.).
Lopes CB. et al., "Infrared Laser Photobiomodulation (lambda 830 nm) on Bone Tissue Around Dental Implants: a Raman Spectroscopy and Scanning Electronic Microscopy Study in Rabbits", Photomed Laser Surg. Apr. 2007, 25(2):96-101, Abstract, (1pp.).
Kim KH, et al., "Laser Lipolysis Using a Novel 1,064nm Nd:YAG Laser", Dermatol Surg. Feb. 2006; 32(2) :241-48: discussion 247, (1pp.).
Kim HS, et al., "Endovenous Laser Ablation of the Great Saphenous Vein with a 980-nm Diode Laser in Continuous Mode: Early Treatment Failures and Successful Repeat Treatments", Comment in: J. Vasc. Interv Radiol, Jun. 2007; 18(6):811; Author Reply 812-3, (2pp.).
Heinrich E., et al, "Technique and Short-Term Outcome of Green Light Laser (KTP, 80w) Vaporisation of the Prostate", Eur Urol. Dec. 2007;52 (6):1632-7, Epub Jul. 31, 2007, (1pp.).
Liu, Timon et al., "Photobiomodulation: Phenomenology and its Mechanism" (c) 2005; SPIE—The International Society for Optical Engineering, Abstract, downloaded from http://adsabs.harvard.edu/abs/2005SPIE.5630..185L on Mar. 26, 2008 (1pp.).
Han X, et al., "Multiple-color Optical Activation, Silencing, and Desynchronization of Neural Activity, with Single-Spike Temporal Resolution", PLoS One, Mar. 21, 2007; 2(3):e299, Abstract, downloaded form www.ncbi.nlm.nih.gov on Apr. 2, 2008, (1pp.).
N.I.Smith et al., "Photostimulation of Two Types of $Ca^{2+}$ Waves in Rat Pheochoromocytoma PC12 Cells by Ultrashort Pulsed Near-infrared Laser Irradiation", Laser Physics Letters, vol. 3, Issue 3, pp. 154-16, published online Oct. 13, 2005, downloaded from http://www.3.interscience.wiley.com on Mar. 4, 2008, Abstract, (1pp.).
Katz LC, et al., "Scanning Laser Photostimulation: A New Approach for analyzing Brain Circuits", J. Neurosci Methods, Oct. 1994;54 (2):205-18, Abstract, downloaded from http://www.ncbi.nlm.nih.gov/pubmed/7869753 on Mar. 4, 2008, (1pp.).
Cha-Min Tang, "Unit 6.21 Photolysis of Caged Neurotransmitters: Theory and Procedures for Light Delivery", InterScience, Baltimore VA Medical Center and University of Maryland School of Medicine, Abstract, 2006, (1pp.).

Godwin DW, et al., "Photostimulation with Caged Neurotransmitters Using Fiber Optic Lightguides", J. Neurosci Methods, Apr. 25, 1997:73(1):91-106, Abstract, http://www.ncbi.nlm.nih.gov/pubmed/9130682 , (1 pp.).
Kadir Asian et al., "Multicolor Microwave-Triggered Metal-Enhances Chemiluminescence", JACS Communication, J. Am. Chem. Soc., online published Sep. 23, 2006, (6pp.).
F.V. Santos et al., "Photocatalysts as a Tertiary Treatment for Petroleum Refinery Wastewaters", Brazilian Journal of Chemical Engineering, vol. 23, No. 4, Oct.-Dec. 2006, pp. 451-460, www.abeg.org.br/bjche , (10pp.).
Mai Thu Thi Tran et al., "Ultraviolet Treatment of Orange Juice", Elsevier, Innovative Food Science and Emerging Technologies 5 (2004), pp. 495-502, www.s.sciencedirect.com , (8pp.).
M. Thoms[a0] et al., "Method for the determination of Photostimulable defect Center Concentrations, Production Rates, and Effective Formation Energies", J. Appl. Phys. 75 (9), May 1, 1994, (4pp.).
Surbhl Lal et al., "Nano-optics from Sensing to Waveguiding", Review Article, Nature Photonics, vol. 1, Nov. 2007, pp. 641-648, www.nature.com/naturephotonics, (8pp.).
Mustafa H. Chowdhury et al., "Metal-Enhanced Fluorescence of Phycobiliprotein from Heterogeneous Plasmonic Nanostructures", J. Phys. Chem. C 2007, 111, pp. 18856-18863, Articles, (8pp.).
Harry A. Atwater, "The Promise of Plasmonics", Scientific American, published Apr. 2007, www.sciam.com, (8pp.).
Stefan A. Maier, "Plasmonic Field Enhancement and SERS in the Effective Mode Volume Picture", Optics Express, Mar. 6, 2006/ vol. 14, No. 5, pp. 1957-1964, (8pp.).
De Bary Aqua—UV, "Sterilizers for Frest or Marine Water Aquarium, Garden Ponds, Breeder Tanks and Commercial Applications in the Molluscan Shellfish Industry", Info. A4-GB-Nov. 2002, (4pp.).
Loctite. Light, Cure, Technology, Loctite Americas 2000, Technical Manual , www.loctite.com, (24pp.).
Dr. Roger McCartney, Consultant, Fusion UV Systems, Inc., "UV Cocooning: CMTI Emissions Testing Results", Composites 2002 Convention and Trade Show Composites Fabricators Association, Sep. 25-27, 2002, Atlanta, Georgia USA, (11pp.).
Aaron P. VanDevender el al., "Quantum Transduction Via Frequency Upconversion" (Invited), J. Opt. Soc. Am., vol. 24, No. 2, Feb. 2007, pp. 295-297, (5pp.).
Asian Kadir et al., "Fast and Sensitive DNA Hybridization Assays Using Microwave-accelerated Metal-enhanced Fluorescence", ScienceDirect, Biochemical and Biophysical Research Communications 348 (2006) pp. 612-617, www.sciencedirect.com, (6pp.).
Shaomin Wang et al., "Electromagnetic Excitation of Nano-carbon in Vacuum", Optics Express, May 16, 2005, vol. 13, No. 10, 3625, (6pp.).
Kadir Asian et al., "Microwave-Accelerated Metal-Enhanced Fluorescence (MAMEF) with Silver Colloids in 96-well Plates: Application to Ultra Fast and Sensitive Immunoassays, High Throughput Screening and Drug Discovery", Journal of Immunological Method 312 (2006) pp. 137-147, (11pp.).
David J. Hurrell, Sterilization, "Recent Developments in Sterilization Technology", Medical Device Link, The Online Information Source for the Medical Device Industry, Medical Plastics and Biomaterials Magazine PB Article Index, published Sep. 1998, downloaded from http://www.devicelink.com/mpb/archive/98/09/002.html, on May 19, 2008, (8pp.).
"Viral Inactivation of Blood Products", Transfusion, The Journal of The American Association of Blood Banks, vol. 30, Jul./Aug. 1990, No. 6, (3pp.).
N. Elmnasser et al., "Pulsed-light System as a Novel Food Decontamination Technology: a Review", Can. J. Microbiol., 53, (2007), pp. 813-821, (9pp.).
Parmeswaran Diagaradjane et al., "Modulation of in Vivo Tumor Radiation Response Via Gold Nanoshell-Mediated Vascular_Focused Hyperthermia: Characterizing an Integrated Antihypoxic and Localized Vascular Disrupting Targeting Strategy", Nano Letters, 2008, vol. 8, No. 5, 1492-1500, (9PP.).

(56) References Cited

OTHER PUBLICATIONS

Marino A. Campo et al., "Polymeric Photosensitizer Prodrugs for Photodynamic Therapy" Photochemistry and Photobiology, 2007, 83, pp. 958-965, (8PP.)

Competitive Binging Data with one Class of Receptors, Fitting data to a one-site competitive binding curve, http://www.graphpad.com/curvefit/one_kind_of_receptor.htm , 1999, (3pp.).

Jacky Lyden, "Good Vibrations Emanate from Nanotube", NPR, Nov. 5, 2007, downloaded from http://www.npr.org/templates/story/story.php?storyId=15868800 on Nov. 5, 2007, (5pp.).

Martina E. Wieder et al., "Intracellular Photodynamic Therapy with Photosensitizer-nanoparticle Conjugates: Cancer Therapy Using a 'Trojan horse'", The Royal Society of Chemistry and Owner Societies, Photochemical & Photobiol.l Sci., 2006, 5, pp. 727-734, www.rsc.org/pps , (8pp.).

Xiaohue Huang et al., "Plasmonic Photothermal Therapy (PPTT) Using Gold Nanoparticles", Review Article, Laser Med. Sci., 2007, (12pp.).

Ernst Wagner, "Programmed Drug Delivery: Nanosystems for Tumor Targeting", Editorial, Expert Opinion Biol. Ther. 2007, 7(5), pp. 587-593, (7pp.).

Giuseppe Palumbo, "Photodynamic Therapy and Cancer: a Brief Sightseeing Tour", Review, Expert Opinion, Drug Deliv. 2007, 4(2), pp. 131-148, (18pp.).

Sehoon Kim et al., "Organically Modified Silica Nanoparticles Co-encapsulating Photosensitizing Drug and Aggregation-Enhances Two-Photon Absorbing Fluorescent Dye Aggregates for Two-Photon Photodynamic Therapy", JACS Articles, J. Am. Chem. Soc., vol. 129, No. 9, 2007, (8pp.).

Ivan Charamisinau et al., "Semiconductor Laser Insert with Uniform Illumination for Use in Photodynamic Therapy", Applied Optics, Aug. 20, 2005, vol. 44, No. 24, pp. 5055-5068, (14pp.).

Brian M. Caullum, "Smart Medical and Biomedical Sensor Technology", Spie Proceeding Series—The International Society for Optical Engineering, vol. 5261, Oct. 28-29, 2003, (14pp.).

Akimichi Morita et al, "Evidence that Singlet Oxygen-Induced Human T. Helper Cell Apoptosis Is the Basic Mechanism of Ultraviolet-A Radiation Phototherapy", Brief Definitive Report, J. Exp. Med., vol. 186, No. 10, Nov. 17. 1997, pp. 1763-1768, downloaded from http://www.jem.org on Sep. 6, 2007, (6pp.).

M. F. Nichols et al., "Oxygen Diffusion and Reaction Kinetics in the Photodynamic Therapy of Multicell Tumour Speroid", Phys. Med. Biol. 39, 1994, 2161-2181, (21pp.).

H. Peter Van Iperen et al., "Singlet Oxygen Producing Photosensitizers in Photophoresis", Journal of Photochemistry and Photobiology B: Biology 38, 1997, pp. 203-208, (6pp.).

Irene Georgakoudi et al. "The Mechanism of Photofrin® Photobleaching and Its Consequences for Photodynamic Dosimetry", Photochemistry and Photobiology, 1997, 65(1) , pp. 135-144, 10pp.).

Brian W. Pogue et al.,"A Photobiological and Photophysical-based Study of Phototoxicity of Two Chlorins[1]", Cancer Research 61, Jan. 15, 2001, pp. 717-724, (8pp.).

Wei Chen et al., "Using Nanoparticles to Enable Simultaneous Radiation and Photodynamic Therapies for Cancer Treatment", J. Nanoscience Nanotechnology, 2006, vol. 6, No. 4, pp. 1159-1166, (8pp.).

Junkoh Yamamoto et al., "Monitoring of Singlet Oxygen Is Useful for Predicting the Photodynamic Effects in the Treatment for Experimental Glioma", Clin Cancer Res 2006: 12(23) Dec. 1, 2008, pp. 7132-7139, www.aacrjournals.org, (10pp.).

Jurgen Baier et al, "Direct Detection of Singlet Oxygen Generated by UVA Irradiation in Human Cells and Skin", Original Article, Journal of Investigative Dermatology, 2007, vol. 127, pp. 1498-1506, (9pp.).

Timothy C. Zhu, "Modeling of Singlet Oxygen During Photodynamic Therapy Using COMSOL Multiphysics", Expert from the Proceedings of the COMSOL Users Conference 2006 Boston, (5pp.).

Fernando L. Primo et al., "Magnetic Nanoemulsions as Drug Delivery System for Foscan : Skin Permeation and retension in Vitro Assays for Topical Application in Photodynamic Therapy (PDT) of Skin Cancer", Journal of Magnetism and Magnetic Materials 311, (2007), pp. 354-357, available online at www.sciencedirect.com , (5pp.).

Harry A. Atwater, "The Promise of Plasmonics, a Technology the Squeezed Electromagnetic Waves into Minuscule Structures May Yield a New Generation of Superfast Computer Chips and Ultrasensitive Molecular Detectors", Scientific American Magazine—Mar. 18, 2007, http://www.sciam.com/article.cfm?id=the-promise-of-plasmonics&pring=true , (4pp.).

Camaro C, Pathak MA., "Studies on the Nature of In Vitro and In Vivo Photosensitization Reactions by Psoralens and Porphyrins", J. Invest Dermatol. 1988, Mach 90(3) pp. 267-275, Abstract, (1 pp.).

Paul D. Wood et al., "Reactions of Psoralen Radical Cations with Biological Substrates", Photochemistry and Photobiology, Article, pp. 155-162 (Abstract), Bioone Online Journal Access Control, vol. 72, Jun. 2008, http://www.bioone.org/perlserv , 1pp.).

Reynel Cando et al., "High Potency of Indolyl Aryl Sulfone nonnucleoside Inhibitors Towards Drug-Resistant Human Immunodefidency Virus Type 1 Reverse Transcriptase Mutants Is Due to Selective Targeting of Different Mechanistic Form of the Enzyme", Antimicrobial Agents and Chemotherapy,vol. 49, No. 11, Nov. 2005, pp. 4546-4554 downloaded from aac.asm.org on Oct. 17, 2007, (9pp.).

Jacek Bartkowiak et al., "Selective Displacement of Nuclear Proteins by Antitumor Drugs Having Affinity for Nucleic Acids", Proc.Natl. Acad.Sci. vol. 86, pp. 5151-5154, Jul. 1989, Medical Sciences, Abstract, (1pp.).

Sylvie Giacchetti et al., "Phase III Trial Comparing 4-Day Chronomodulated Therapy Versus 2-Day Conventional Delivery of Fluorouracil, Leucovorin, and Oxaliplatin As First-Line Chemotherapy of Metastatic Colorectal Cancer: The European Organisation for Research and Treatment of Cancer Chronotherapy Group", Journal of Clinical Oncology, Original Report, vol. 24, No. 22, Aug. 1, 2008, (8pp.).

Fr G. McConnell, "Visit to Lassie (Apr. 2008): Initiating an International Colaboration to Develop Laser Sources for Spatially-Localised, Deep-Tissue Photostimulation", University of Strathclyde, Centre for Biophotonics, EPSRC Reference: EP/F036213/1, EPDRC, http://gow.epsrc.ac.uk/ViewGrant.aspx?GrantRef=EP/F036213/1 (2pp.).

Combined Chinese Office Action and Search Report issued Dec. 5, 2012, in Patent Application No. 200880019254.0 (with English-language translation).

Japanese Office Action issued Dec. 18, 2012, in Patent Application No. 2010-503137 (with English-language translation).

Theodossis Theodossiou, et al., "Firefly Luciferin-activated Rose Bengal: In Vitro Photodynamic Therapy by Intracellular Chemiluminescence in Transgenic NIH 3T3 Cells", Cancer Research, vol. 63, No. 8, Apr. 15, 2003, pp. 1818-1821.

Thai Office Action issued Dec. 30, 2010, in Patent Application No. 0801001775.

Schaffer et al. Journal of Photochemistry and Photobiology B: Biology, 2002, vol. 66, pp. 157-164.

Office Action issued Nov. 24, 2011, in Chinese Patent Application No. 200880019254.0 (English translation only).

Chilean Office Action issued Oct. 17, 2011, in Patent Application No. 997-08.

Office Action issued May 25, 2012 in Australian Application No. 2008237121.

Third Office Action issued May 30, 2013, in Chinese patent application No. 200880019254.0 (w/English translation).

Callaway et al, "Photostimulation using caged glutamate reveals functional circuitry in living brain slices", Proc. Natl. Acad. Sci. USA, vol. 90, Aug. 1993, pp. 7661-7665.

Office Action issued Sep. 26, 2013 in Chinese Patent Application No. 200880019254.0 (with English-language translation).

Office Action issued Jan. 21, 2014 in Japanese Patent Application 2010-503137.

Thai Office Action issued Dec. 18, 2013 in Patent Application No. 0801001775.

(56) References Cited

OTHER PUBLICATIONS

Office Action issued Feb. 27, 2017, in European patent application No. 08 733 147.6.
Office Action issued Feb. 1, 2017, in Chilean patent application No. 2015-382 (w/English translation).
Office Action issued Feb. 1, 2017, in Chilean patent application No. 2015-383 (w/English translation).
Final Office Action issued Apr. 2, 2017, in Korean patent application No. 10-2014-7032340 (w/English translation).
Office Action issued Apr. 2, 2017, in Korean patent application No. 10-2017-7002804 (w/English translation).

\* cited by examiner

METHODS AND SYSTEMS FOR TREATING CELL PROLIFERATION RELATED DISORDERS

CROSS REFERENCE TO RELATED APPLICATIONS

This application is a Continuation of U.S. application Ser. No. 11/935,655, filed Nov. 6, 2007, and claims priority from Provisional Application Ser. No. 60/910,663, filed Apr. 8, 2007, entitled "METHOD OF TREATING CELL PROLIFERATION DISORDERS," the contents of which are hereby incorporated herein by reference.

BACKGROUND OF THE INVENTION

Field of Invention

The present invention relates to methods and systems for treating cell proliferation disorders, that provide better distinction between normal, healthy cells and those cells suffering a cell proliferation disorder (hereafter "target cells") and preferably that can be performed using non-invasive or minimally invasive techniques.

Discussion of the Background

Cell Proliferation Disorders

There are several types of cell proliferation disorders. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Of these, cancer is perhaps the most well known. The term "cancer" generally refers to a diverse class of diseases that are commonly characterized by an abnormal proliferation of the diseased cells. A unifying thread in all known types of cancer is the acquisition of abnormalities in the genetic material of the cancer cell and its progeny. Once a cell becomes cancerous, it will proliferate without respect to normal limits, invading and destroying adjacent tissues, and may even spread to distant anatomic sites through a process called metastasis. These life-threatening, malignant properties of cancers differentiate them from benign tumors, which are self-limited in their growth and do not invade or metastasize.

The impact of cancer on society cannot be overstated. The disease may affect people at all ages, with a risk factor that significantly increases with a person's age. It has been one of the principal causes of death in developed countries and, as our population continues to age, it is expected to be an even greater threat to our society and economy. Therefore, finding cures and effective treatments for cancer has been, and remains, a priority within the biomedical research community.

Treatment Methods

Existing treatments for cell proliferation disorders such as cancer include surgery, chemotherapy, radiation therapy, immunotherapy, monoclonal antibody therapy, and several other lesser known methods. The choice of therapy usually depends on the location and severity of the disorder, the stage of the disease, as well as the patient's response to the treatment.

While some treatments may only seek to manage and alleviate symptoms of the disorder, the ultimate goal of any effective therapy is the complete removal or cure of all disordered cells without damage to the rest of the body. With cancer, although surgery may sometimes accomplish this goal, the propensity of cancer cells to invade adjacent tissue or to spread to distant sites by microscopic metastasis often limits the effectiveness of this option. Similarly, the effectiveness of current chemotherapy is often limited by toxicity to other tissues in the body. Radiation therapy suffers from similar shortcomings as other aforementioned treatment methods. Most of these cancer treatment methods, including radiation therapy, are known to cause damage to DNA, which if not repaired during a critical stage in mitosis, the splitting of the cell during cell proliferation, leads to a programmed cell death, i.e. apoptosis. Further, radiation tends to damage healthy cells, as well as malignant tumor cells.

A number of patents describe ex vivo treatment of bodily fluids, for example blood. Blood is obtained from a patient, treated with a photosensitive agent, exposed to UV radiation, and reinjected to the patient (i.e. extracorporeal photopheresis). Alternatively, a patient can be treated in vivo with a photosensitive agent followed by the withdrawal of a sample from the patient, treatment with UV radiation in vitro (ex vivo), and reinjecting the patient with the treated sample. This method is known for producing an autovaccine. A method of treating a patient with a photosensitive agent, exposing the patient to an energy source and generating an autovaccine effect wherein all steps are conducted in vivo has not been described. See WO 03/049801, U.S. Pat. No. 6,569,467; U.S. Pat. No. 6,204,058; U.S. Pat. No. 5,980,954; U.S. Pat. No. 6,669,965; U.S. Pat. No. 4,838,852; U.S. Pat. No. 7,045,124, and U.S. Pat. No. 6,849,058. Moreover, the side effects of extracorporeal photopheresis are well known and include nausea, vomiting, cutaneous erythema, hypersensitivity to sunlight, and secondary hematologic malignancy. Researchers are attempting to use photopheresis in experimental treatments for patients with cardiac, pulmonary and renal allograft rejection; autoimmune diseases, and ulcerative colitis.

A survey of known treatment methods reveals that these methods tend to face a primary difficulty of differentiating between normal cells and target cells when delivering treatment, often due to the production of singlet oxygen which is known to be non-selective in its attack of cells, as well as the need to perform the processes ex vivo, or through highly invasive procedures, such as surgical procedures in order to reach tissues more than a few centimeters deep within the subject.

U.S. Pat. No. 5,829,448 describes simultaneous two photon excitation of photo-agents using irradiation with low energy photons such as infrared or near infrared light (NRI). A single photon and simultaneous two photon excitation is compared for psoralen derivatives, wherein cells are treated with the photo agent and are irradiated with NRI or UV radiation. The patent suggests that treating with a low energy irradiation is advantageous because it is absorbed and scattered to a lesser extent than UV radiation. However, the use of NRI or UV radiation is known to penetrate tissue to only a depth of a few centimeters. Thus any treatment deep within the subject would necessarily require the use of ex vivo methods or highly invasive techniques to allow the irradiation source to reach the tissue of interest.

Chen et al., J. Nanosci. and Nanotech., 6:1159-1166 (2006); Kim et al., JACS, 129:2669-2675 (2007); U.S. 2002/0127224; and U.S. Pat. No. 4,979,935 each describe methods for treatment using various types of energy activation of agents within a subject. However, each suffers from the drawback that the treatment is dependent on the production of singlet oxygen to produce the desired effect on the tissue being treated, and is thus largely indiscriminate in affecting both healthy cells and the diseased tissue desired to be treated.

U.S. Pat. No. 6,908,591 discloses methods for sterilizing tissue with irradiation to reduce the level of one or more active biological contaminants or pathogens, such as viruses, bacteria, yeasts, molds, fungi, spores, prions or similar agents responsible, alone or in combination, for transmissible spongiform encephalopathies and/or single or multicellular parasites, such that the tissue may subsequently be used in transplantation to replace diseased and/or otherwise defective tissue in an animal. The method may include the use of a sensitizer such as psoralen, a psoralen-derivative or other photosensitizer in order to improve the effectiveness of the irradiation or to reduce the exposure necessary to sterilize the tissue. However, the method is not suitable for treating a patient and does not teach any mechanisms for stimulating the photosensitizers, indirectly.

U.S. Pat. No. 6,235,508 discloses antiviral applications for psoralens and other photoactivatable molecules. It teaches a method for inactivating viral and bacterial contaminants from a biological solution. The method includes mixing blood with a photosensitizer and a blocking agent and irradiating the mixture to stimulate the photosensitizer, inactivating substantially all of the contaminants in the blood, without destroying the red blood cells. The blocking agent prevents or reduces deleterious side reactions of the photosensitizer, which would occur if not in the presence of the blocking agent. The mode of action of the blocking agent is not predominantly in the quenching of any reactive oxygen species, according to the reference.

Also, U.S. Pat. No. 6,235,508 suggests that halogenated photosensitizers and blocking agents might be suitable for replacing 8-methoxypsoralen (8-MOP) in photophoresis and in treatment of certain proliferative cancers, especially solid localized tumors accessible via a fiber optic light device or superficial skin cancers. However, the reference fails to address any specific molecules for use in treating lymphomas or any other cancer. Instead, the reference suggests a process of photophoresis for antiviral treatments of raw blood and plasma.

U.S. Pat. No. 6,235,508 teaches away from 8-MOP and 4'-aminomethyl-4,5',8-trimethylpsoralen (AMT) and many other photoactivatable molecules, which are taught to have certain disadvantages. Fluorescing photosensitizers are said to be preferred, but the reference does not teach how to select a system of fluorescent stimulation or photoactivation using fluorescent photosensitizers. Instead, the fluorescing photosensitizer is limited to the intercalator that is binding to the DNA. The reference suggests that fluorescence indicates that such an intercalator is less likely to stimulate oxygen radicals. Thus, the reference fails to disclose any mechanism of photoactivation of an intercalator other than by direct photoactivation by UV light, although use of a UV light probe or X-rays is suggested for penetrating deeper into tissues. No examples are provided for the use of a UV light probe or for use of X-rays. No example of any stimulation by X-ray radiation is taught.

Psoralens and Related Compounds

U.S. Pat. No. 6,235,508 further teaches that psoralens are naturally occurring compounds which have been used therapeutically for millennia in Asia and Africa. The action of psoralens and light has been used to treat vitiligo and psoriasis (PUVA therapy; Psoralen Ultra Violet A). Psoralen is capable of binding to nucleic acid double helices by intercalation between base pairs; adenine, guanine, cytosine and thymine (DNA) or uracil (RNA). Upon sequential absorption of two UV-A photons, psoralen in its excited state reacts with a thymine or uracil double bond and covalently attaches to both strands of a nucleic acid helix. The cross-linking reaction appears to be specific for a thymine (DNA) or a uracil (RNA) base. Binding proceeds only if psoralen is intercalated in a site containing thymine or uracil, but an initial photoadduct must absorb a second UVA photon to react with a second thymine or uracil on the opposing strand of the double helix in order to crosslink each of the two strands of the double helix, as shown below. This is a sequential absorption of two single photons as shown, as opposed to simultaneous absorption of two or more photons.

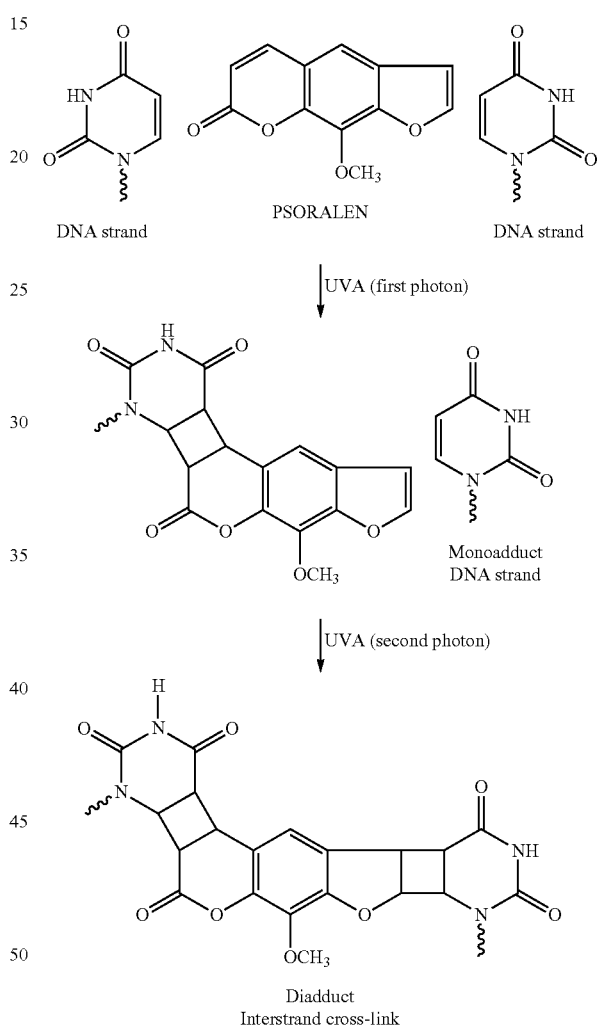

In addition, the reference teaches that 8-MOP is unsuitable for use as an antiviral, because it damages both cells and viruses. Lethal damage to a cell or virus occurs when the psoralen is intercalated into a nucleic acid duplex in sites containing two thymines (or uracils) on opposing strands but only when it sequentially absorbs 2 UVA photons and thymines (or uracils) are present. U.S. Pat. No. 4,748,120 of Wiesehan is an example of the use of certain substituted psoralens by a photochemical decontamination process for the treatment of blood or blood products.

Additives, such as antioxidants are sometimes used with psoralens, such as 8-MOP, AMT and I-IMT, to scavenge singlet oxygen and other highly reactive oxygen species formed during photoactivation of the psoralens. It is well known that UV activation creates such reactive oxygen species, which are capable of seriously damaging otherwise healthy cells. Much of the viral deactivation may be the result of these reactive oxygen species rather than any effect of photoactivation of psoralens. Regardless, it is believed that no auto vaccine effect has been observed.

The best known photoactivatable compounds are derivatives of psoralen or coumarin, which are nucleic acid intercalators. The use of psoralen and coumarin photosensitizers can give rise to alternative chemical pathways for dissipation of the excited state that are either not beneficial to the goal of viral inactivation, or that are actually detrimental to the process. For psoralens and coumarins, this chemical pathway is likely to lead to the formation of a variety of ring-opened species, such as shown below for coumarin:

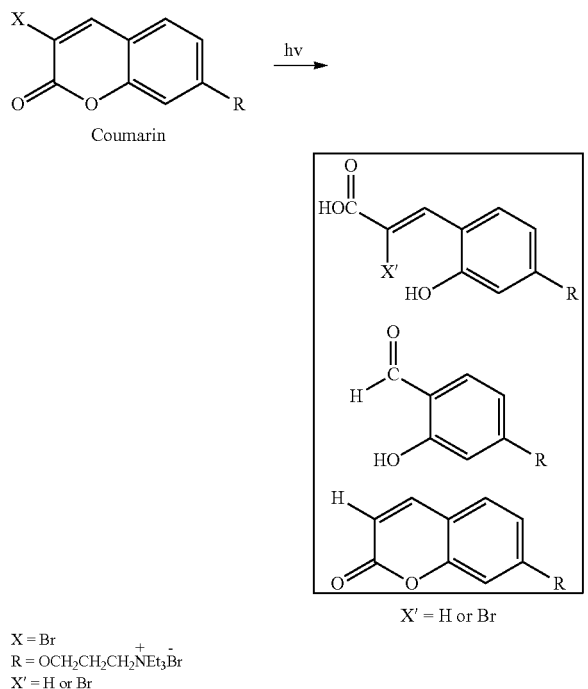

X = Br
R = OCH$_2$CH$_2$CH$_2$NEt$_3^+$Br$^-$
X' = H or Br

Research in this field over-simplifies mechanisms involved in the photoactivating mechanism and formation of highly reactive oxygen species, such as singlet oxygen. Both may lead to inactivating damage of tumor cells, viruses and healthy cells. However, neither, alone or combined, lead to an auto vaccine effect. This requires an activation of the body's own immune system to identify a malignant cell or virus as threat and to create an immune response capable of lasting cytotoxic effects directed to that threat. It is believed, without being limiting in any way, that photoactivation and the resulting apoptosis of malignant cells that occurs in extracorporeal photophoresis causes the activation of an immune response with cytotoxic effects on untreated malignant cells. While the complexity of the immune response and cytotoxid effects is fully appreciated by researchers, a therapy that harnesses the system to successfully stimulate an auto vaccine effect against a targeted, malignant cell has been elusive, except for extracorporeal photophoresis for treating lymphoma.

Midden (W. R. Midden, Psoralen DNA photobiology, Vol II (ed. F. P. Gaspalloco) CRC press, pp. 1. (1988) has presented evidence that psoralens photoreact with unsaturated lipids and photoreact with molecular oxygen to produce active oxygen species such as superoxide and singlet oxygen that cause lethal damage to membranes. U.S. Pat. No. 6,235,508 teaches that 8-MOP and AMT are unacceptable photosensitizers, because each indiscriminately damages both cells and viruses. Studies of the effects of cationic side chains on furocoumarins as photosensitizers are reviewed in Psoralen DNA Photobiology, Vol. I, ed. F. Gaspano, CRC Press, Inc., Boca Raton, Fla., Chapter 2. U.S. Pat. No. 6,235,508 gleans the following from this review: most of the amino compounds had a much lower ability to both bind and form crosslinks to DNA compared to 8-MOP, suggesting that the primary amino functionality is the preferred ionic species for both photobinding and crosslinking.

U.S. Pat. No. 5,216,176 of Heindel discloses a large number of psoralens and coumarins that have some effectiveness as photoactivated inhibitors of epidermal growth factor. Halogens and amines are included among the vast functionalities that could be included in the psoralen/coumarin backbone. This reference is incorporated herein by reference.

U.S. Pat. No. 5,984,887 discloses using extracorporeal photophoresis with 8-MOP to treat blood infected with CMV. The treated cells as well as killed and/or attenuated virus, peptides, native subunits of the virus itself (which are released upon cell break-up and/or shed into the blood) and/or pathogenic noninfectious viruses are then used to generate an immune response against the virus, which was not present prior to the treatment.

Photodynamic Therapy (PDT)

Photodynamic therapy (PDT) is a treatment modality that uses a photosensitizing agent and laser light to kill cells. PDT retains several photosensitizers in tumors for a longer time than in normal tissues, thus offering potential improvement in treatment selectivity. See Comer C., "Determination of [3H]- and [14C] hematoporphyrin derivative distribution in malignant and normal tissue," Cancer Res 1979, 39: 146-151; Young S W, et al., "Lutetium texaphyrin (PCI-0123) a near-infrared, water-soluble photosensitizer," Photochem Photobiol 1996, 63:892-897; and Berenbaum M C, et al., "Meso-Tetra(hydroxyphenyl)porphyrins, a new class of potent tumor photosensitisers with favourable selectivity," Br J Cancer 1986, 54:717-725. Photodynamic therapy uses light of a specific wavelength to activate the photosensitizing agent. Various light sources have been developed for PDT that include dye lasers and diode lasers. Light generated by lasers can be coupled to optical fibers that allow the light to be transmitted to the desired site. See Pass 1-11, "Photodynamic therapy in oncology: mechanisms and clinical use," J Natl Cancer Inst 1993, 85:443-456. According to researchers, the cytotoxic effect of PDT is the result of photooxidation reactions, as disclosed in Foote C S, "Mechanisms of photooxygenation," Proa Clin Biol Res 1984, 170:3-18. Light causes excitation of the photosensitizer, in the presence of oxygen, to produce various toxic species, such as singlet oxygen and hydroxyl radicals. It is not clear that direct damage to DNA is a major effect; therefore, this may indicate that photoactivation of DNA crosslinking is not stimulated efficiently.

Furthermore, when laser light is administered via external illumination of tissue surfaces, the treatment effect of PDT is confined to a few millimeters (i.e. superficial). The reason for this superficial limitation is mainly the limited penetration of the visible light used to activate the photosensitizer. Thus, PDT is used to treat the surfaces of critical organs, such as lungs or intra-abdominal organs, without damage to the underlying structures. However, even these treatments require significantly invasive techniques to treat the surface of the affected organs. Clinical situations use the procedure in conjunction with surgical debulking to destroy remnants of microscopic or minimal gross disease. It is possible that the laser light and small amount of remaining microscopic and minimal gross disease results in too little or highly damaged structures. Pre-clinical data show that some immune response is generated, but clinical trials have reported no auto vaccine effect similar to that produced by extracorporeal photophoresis in clinical conditions. Instead, immune response appears to be vigorous only under limited conditions and only for a limited duration.

Problems

It is well recognized that a major problem associated with the existing methods of diagnosis and treatment of cell proliferation disorders is in differentiation of normal cells from target cells. Such target specificity is difficult to achieve by way of surgery since the strategy there is simply to cut out a large enough portion of the affected area to include all diseased cells and hope that no diseased cells have spread to other distant locations.

With chemotherapy, while some degree of differentiation can be achieved, healthy cells are generally adversely affected by chemo-agents. As in surgery, the treatment strategy in chemotherapy is also to kill off a large population of cells, with the understanding that there are far more normal cells than diseased cells so that the organism can recover from the chemical assault.

Radiation therapy works by irradiating cells with high levels of high energy radiation such as high energy photon, electron, or proton. These high energy beams ionize the atoms which make up a DNA chain, which in turn leads to cell death. Unlike surgery, radiation therapy does not require placing patients under anesthesia and has the ability to treat tumors deep inside the body with minimal invasion of the body. However, the high doses of radiation needed for such therapies damages healthy cells just as effectively as it does diseased cells. Thus, similar to surgery, differentiation between healthy and diseased cells in radiation therapy is only by way of location. There is no intrinsic means for a radiation beam to differentiate between a healthy cell from a diseased cell either.

Other methods may be more refined. For example, one form of advanced treatment for lymphoma known as extra-corporeal photophoresis involves drawing the patient's blood from his body into an instrument where the white cells (buffy coat) are separated from the plasma and the red blood cells. A small amount of the plasma separated in this process is then isolated and mixed with a photosensitizer (PS), a drug that can be activated by light. The buffy coat is then exposed to a light to activate the drug. The treated blood is then returned to the patient. In this example, one may think of the target-specificity problem as being solved by separating the blood from the rest of the body where the target components are easily exposed.

However, this procedure has its drawbacks; it requires drawing blood from the patient, thus requiring cumbersome machinery to perform and may require blood transfusion in order to maintain the volume of blood flow in the machine. Further, this also limits the size of the patient that can be treated, since the extracorporeal volume is great and too much withdrawal of blood increases the risk of hypovolemic shock. The method is also limited to treating blood-born cell proliferation related disorders such as lymphoma, and is not capable of treating solid tumors or other types of non-blood related cell proliferation disorders.

A problem encountered in PDT therapy is the inability to treat target areas that are more than a few centimeters beneath the surface of the skin without significant invasive techniques, and the fact that PDT typically operates by generation of sufficient quantities of singlet oxygen to cause cell lysis. However, singlet oxygen in sufficient concentration will lyse not only target cells, but also healthy cells rather indiscriminately.

Therefore, there still exists a need for better and more effective treatments that can more precisely target the diseased cells without causing substantial side-effects or collateral damages to healthy tissues, and which are capable of treating even solid tumors or other types of non-blood related cell proliferation disorders.

SUMMARY OF THE INVENTION

Accordingly, one object of the present invention is to provide a method for the treatment of a cell proliferation disorder that permits treatment of a subject in any area of the body while being non-invasive and having high selectivity for targeted cells relative to healthy cells.

A further object of the present invention is to provide a method for treatment of a cell proliferation disorder which can use any suitable energy source as the initiation energy source to activate the activatable pharmaceutical agent and thereby cause a predetermined cellular change to treat cells suffering from a cell proliferation disorder.

A further object of the present invention is to provide a method for treatment of a cell proliferation disorder using an energy cascade to activate an activatable pharmaceutical agent that then treats cells suffering from a cell proliferation disorder.

A further object of the present invention is to provide a method for generating an autovaccine effect in a subject, which can be in vivo thus avoiding the need for ex vivo treatment of subject tissues or cells, or can be ex vivo.

A further object of the present invention is to provide a computer implemented system for performing the methods of the present invention.

A still further object of the present invention is to provide a kit and a pharmaceutical composition for use in the present invention methods.

These and other objects of the present invention, which will become more apparent in conjunction with the following detailed description of the preferred embodiments, either alone or in combinations thereof, have been satisfied by the discovery of a method for treating a cell proliferation disorder in a subject, comprising:

(1) administering to the subject an activatable pharmaceutical agent that is capable of effecting a predetermined cellular change when activated, either alone or in combination with an energy modulation agent; and (2) applying an initiation energy from an initiation energy source to the subject, wherein the applying activates the activatable agent in situ, thus causing the predetermined cellular change to occur, wherein occurrence of the predetermined cellular change causes an increase or decrease in rate of cell proliferation to treat the cell proliferation related disorder, and a kit for performing the method, a pharmaceutical composition, a computer implemented system for performing the method and a method and system for causing an autovaccine effect in a subject.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
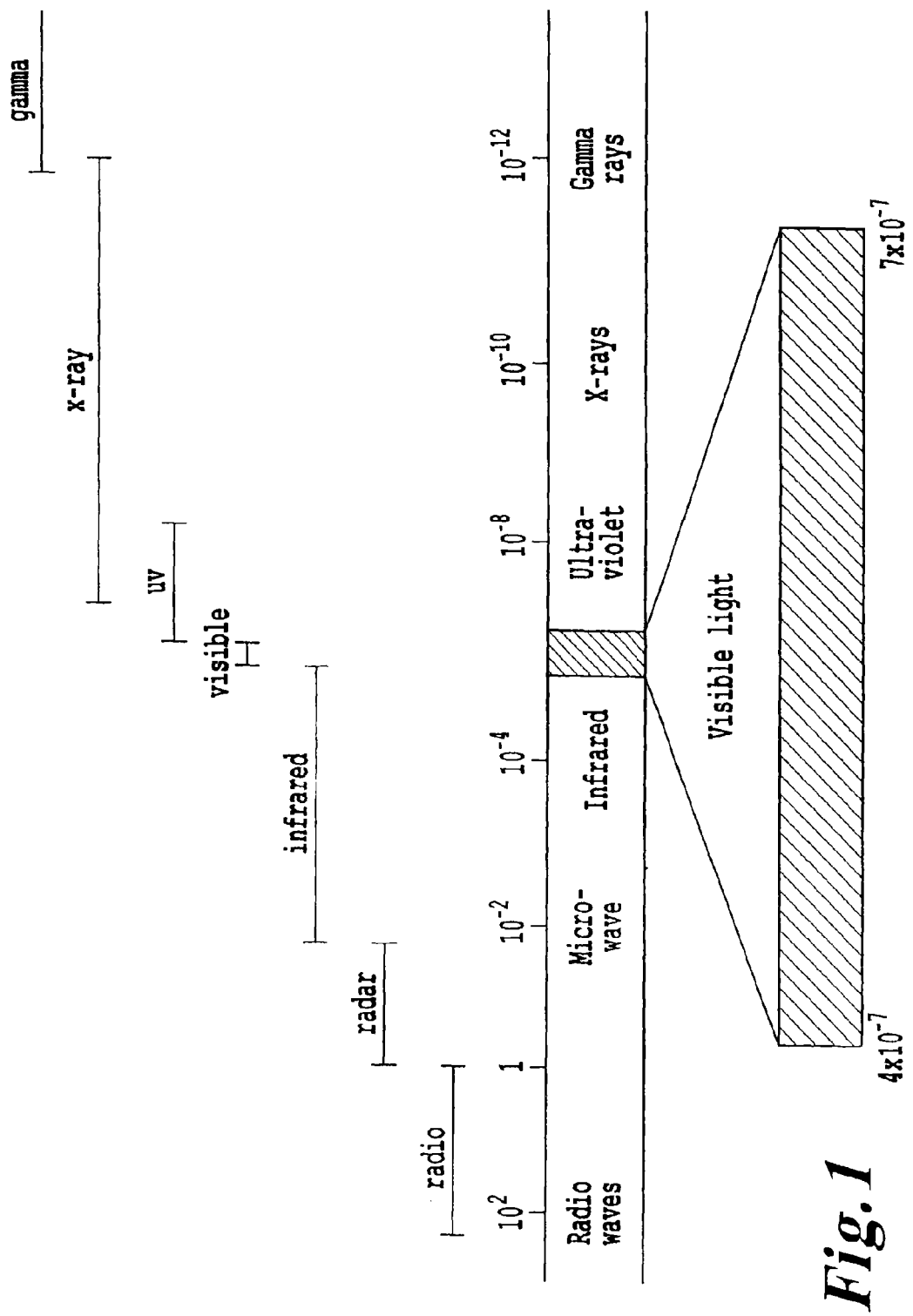
FIG. 1 provides an exemplary electromagnetic spectrum in meters (1 nm equals meters).

The present invention sets forth a novel method of treating cell proliferation disorders that is effective, specific, and has few side-effects. Those cells suffering from a cell proliferation disorder are referred to herein as the target cells. A treatment for cell proliferation disorders, including solid tumors, is capable of chemically binding cellular nucleic acids, including but not limited to, the DNA or mitochondrial DNA or RNA of the target cells. For example, a photoactivatable agent, such as a psoralen or a psoralen derivative, is exposed in situ to an energy source capable of activating the photoactivatable agent or agents selected. In another example, the photoactivatable agent is a photosensitizer. The photoactivatable agent may be a metal nanocluster or a molecule.

As noted above, an object of the present invention is to treat cell proliferation disorders. Exemplary cell proliferation disorders may include, but are not limited to, cancer, as well as bacterial and viral infections where the invading bacteria grows at a much more rapid rate than cells of the infected host. In addition, treatment for certain developmental stage diseases related to cell proliferation, such as syndactyly, are also contemplated.

Accordingly, in one embodiment, the present invention provides methods that are capable of overcoming the shortcomings of the existing methods. In general, a method in accordance with the present invention utilizes the principle of energy transfer to and among molecular agents to control delivery and activation of pharmaceutically active agents such that delivery of the desired pharmacological effect is more focused, precise, and effective than the conventional techniques.

Generally, the present invention provides methods for the treatment of cell proliferation disorders, in which an initiation energy source provides an initiation energy that activates an activatable pharmaceutical agent to treat target cells within the subject. In one preferred embodiment, the initiation energy source is applied indirectly to the activatable pharmaceutical agent, preferably in proximity to the target cells. Within the context of the present invention, the phrase "applied indirectly" (or variants of this phrase, such as "applying indirectly", "indirectly applies", "indirectly applied", "indirectly applying", etc.), when referring to the application of the initiation energy, means the penetration by the initiation energy into the subject beneath the surface of the subject and to the activatable pharmaceutical agent within a subject. In one embodiment, the initiation energy interacts with a previously administered energy modulation agent which then activates the activatable pharmaceutical agent. In another embodiment, the initiation energy itself activates the activatable pharmaceutical agent. In either embodiment, the initiation energy source cannot be within line-of-sight of the activatable pharmaceutical agent. By "cannot be within line-of-sight" is meant that if a hypothetical observer were located at the location of the activatable pharmaceutical agent, that observer would be unable to see the source of the initiation energy.

Although not intending to be bound by any particular theory or be otherwise limited in any way, the following theoretical discussion of scientific principles and definitions are provided to help the reader gain an understanding and appreciation of the present invention.

As used herein, the term "subject" is not intended to be limited to humans, but may also include animals, plants, or any suitable biological organism.

As used herein, the phrase "cell proliferation disorder" refers to any condition where the growth rate of a population of cells is less than or greater than a desired rate under a given physiological state and conditions. Although, preferably, the proliferation rate that would be of interest for treatment purposes is faster than a desired rate, slower than desired rate conditions may also be treated by methods of the present invention. Exemplary cell proliferation disorders may include, but are not limited to, cancer, bacterial infection, immune rejection response of organ transplant, solid tumors, viral infection, autoimmune disorders (such as arthritis, lupus, inflammatory bowel disease, Sjogrens syndrome, multiple sclerosis) or a combination thereof, as well as aplastic conditions wherein cell proliferation is low relative to healthy cells, such as aplastic anemia. Particularly preferred cell proliferation disorders for treatment using the present methods are cancer, *staphylococcus aureus* (particularly antibiotic resistant strains such as methicillin resistant *staphylococcus aureus* or MRSA), and autoimmune disorders.

As used herein, an "activatable pharmaceutical agent" is an agent that normally exists in an inactive state in the absence of an activation signal. When the agent is activated by a matching activation signal under activating conditions, it is capable of effecting the desired pharmacological effect on a target cell (i.e. preferably a predetermined cellular change). Signals that may be used to activate a corresponding agent may include, but are not limited to, photons of specific wavelengths (e.g. x-rays, or visible light), electromagnetic energy (e.g. radio or microwave), thermal energy, acoustic energy, or any combination thereof. Activation of the agent may be as simple as delivering the signal to the agent or may further premise on a set of activation conditions. For example, in the former case, an activatable pharmaceutical agent, such as a photosensitizer, may be activated by UV-A radiation. Once activated, the agent in its active-state may then directly proceed to effect a cellular change. Where activation may further premise upon other conditions, mere delivery of the activation signal may not be sufficient to bring about the desired cellular change. For example, a photoactive compound that achieves its pharmaceutical effect by binding to certain cellular structure in its active state may require physical proximity to the target cellular structure when the activation signal is delivered. For such activatable agents, delivery of the activation signal under non-activating conditions will not result in the desired pharmacologic effect. Some examples of activating conditions may include, but are not limited to, temperature, pH, location, state of the cell, presence or absence of co-factors.

Selection of an activatable pharmaceutical agent greatly depends on a number of factors such as the desired cellular change, the desired form of activation, as well as the physical and biochemical constraints that may apply. Exemplary activatable pharmaceutical agents may include, but are not limited to, agents that may be activated by photonic energy, electromagnetic energy, acoustic energy, chemical or enzymatic reactions, thermal energy, or any other suitable activation mechanisms.

When activated, the activatable pharmaceutical agent may effect cellular changes that include, but are not limited to, apoptosis, redirection of metabolic pathways, up-regulation of certain genes, down-regulation of certain genes, secretion of cytokines, alteration of cytokine receptor responses, or combinations thereof.

The mechanisms by which an activatable pharmaceutical agent may achieve its desired effect are not particularly limited. Such mechanisms may include direct action on a predetermined target as well as indirect actions via alterations to the biochemical pathways. A preferred direct action mechanism is by binding the agent to a critical cellular structure such as nuclear DNA, mRNA, rRNA, ribosome, mitochondrial DNA, or any other functionally important structures. Indirect mechanisms may include releasing metabolites upon activation to interfere with normal metabolic pathways, releasing chemical signals (e.g. agonists or antagonists) upon activation to alter the targeted cellular response, and other suitable biochemical or metabolic alterations.

In one preferred embodiment, the activatable pharmaceutical agent is capable of chemically binding to the DNA or mitochondria at a therapeutically effective amount. In this embodiment, the activatable pharmaceutical agent, preferably a photoactivatable agent, is exposed in situ to an activating energy emitted from an energy modulation agent, which, in turn receives energy from an initiation energy source.

Suitable activatable agents include, but are not limited to, photoactive agents, sono-active agents, thermo-active agents, and radio/microwave-active agents. An activatable agent may be a small molecule; a biological molecule such as a protein, a nucleic acid or lipid; a supramolecular assembly; a nanoparticle; or any other molecular entity having a pharmaceutical activity once activated.

The activatable agent may be derived from a natural or synthetic origin. Any such molecular entity that may be activated by a suitable activation signal source to effect a predetermined cellular change may be advantageously employed in the present invention.

Suitable photoactive agents include, but are not limited to: psoralens and psoralen derivatives, pyrene cholesteryloleate, acridine, porphyrin, fluorescein, rhodamine, 16-diazorcortisone, ethidium, transition metal complexes of bleomycin, transition metal complexes of deglycobleomycin, organoplatinum complexes, alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations, porphyrins, dyes such as neutral red, methylene blue, acridine, toluidines, flavine (acriflavine hydrochloride) and phenothiazine derivatives, coumarins, quinolones, quinones, and anthroquinones, aluminum (111) phthalocyanine tetrasulfonate, hematoporphyrin, and phthalocyanine, and compounds which preferentially adsorb to nucleic acids with little or no effect on proteins. The term "alloxazine" includes isoalloxazines.

Endogenously-based derivatives include synthetically derived analogs and homologs of endogenous photoactivated molecules, which may have or lack lower (1 to 5 carbons) alkyl or halogen substituents of the photosensitizers from which they are derived, and which preserve the function and substantial non-toxicity. Endogenous molecules are inherently non-toxic and may not yield toxic photoproducts after photoradiation.

Table 1 lists some photoactivatable molecules capable of being photoactivated to induce an auto vaccine effect.

TABLE 1

SSET and TTET rate constants for bichromophoric peptides

| Compound | $\Lambda_{ex}$ (nm) | $E_{SSET}$ | $k_s$ of donor (s$^{-1}$) | $k_{SSET}$(s$^{-1}$) | $k_{SSET}$(s$^{-1}$) (Average) | $R_0$ (A) | R(A) | $R_{model}$(A) (Average) | $E_{TTET}$ | $k_{TTET}$ (s$^{-1}$) |
|---|---|---|---|---|---|---|---|---|---|---|
| 1B | 224 | 95.3 | $9.5 \times 10^6$ | $2.44 \times 10^8$ | $1.87 \times 10$ | 14.7 | 9 | 9.5 | | |
|  | 266 | 95 | | $1.6 \times 10^8$ | | | | | 2.5 | $5 \times 10^2$ |
|  | 280 | 94 | | $1.36 \times 10^8$ | | | | | | |
| 1A | 224 | 80 | $9.5 \times 10^6$ | $3.6 \times 10^7$ | $3.67 \times 10^7$ | 14.7 | 11.8 | 14.1 | | |
|  | 266 | 79 | | $3.6 \times 10^7$ | | | | | 2 | $3.6 \times 10^2$ |
|  | 280 | 79 | | $3.6 \times 10^7$ | | | | | | |
| 2B | 224 | 77 | $9.5 \times 10^6$ | $3.1 \times 10^7$ | $3.9 \times 10^7$ | 14.7 | 11.9 | 6.5 | | |
|  | 266 | 81 | | $3.9 \times 10^7$ | | | | | 32 | $9.4 \times 10^3$ |
|  | 280 | 83 | | $4.7 \times 10^7$ | | | | | | |
| 2A | 224 | 69 | $9.5 \times 10^6$ | $2.1 \times 10^7$ | $3 \times 10^7$ | 14.7 | 12.2 | 8.1 | 74.3 | $5.7 \times 10^4$ |
|  | 266 | 80 | | $3.7 \times 10^7$ | | | | | | |
|  | 280 | 77 | | $3.2 \times 10^7$ | | | | | | |

TABLE 1-continued
SSET and TTET rate constants for bichromophoric peptides
| Compound | $\Lambda_{e\lambda}$ (nm) | $E_{SSET}$ | $k_s$ of donor (s$^{-1}$) | $k_{SSET}$(s$^{-1}$) | $k_{SSET}$(s$^{-1}$) (Average) | $R_0$ (A) | R(A) | $R_{model}$(A) (Average) | $E_{TTET}$ | $k_{TTET}$ (s$^{-1}$) |
|---|---|---|---|---|---|---|---|---|---|---|
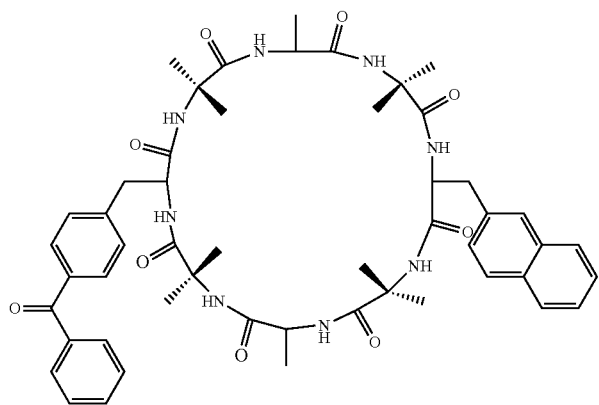
1A
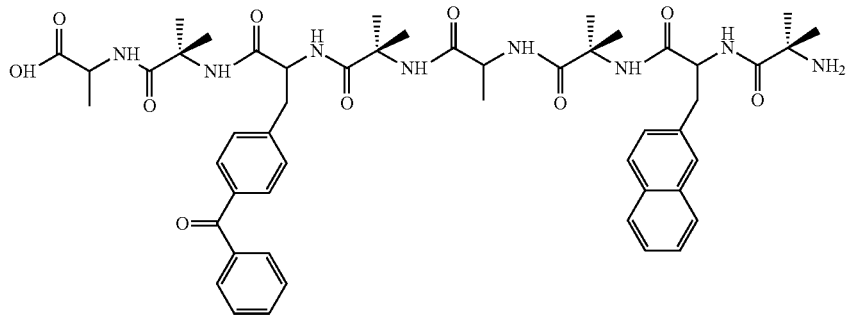
1B
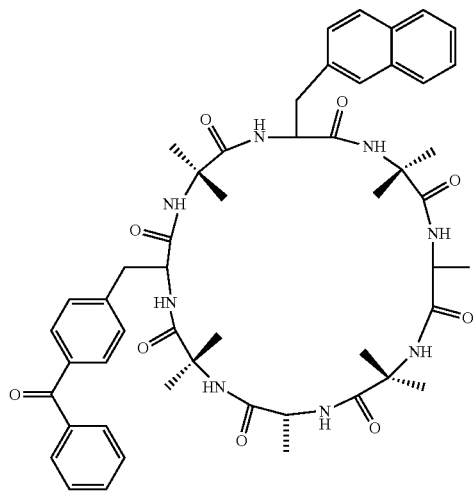
2A TABLE 1-continued SSET and TTET rate constants for bichromophoric peptides

| Compound | $\Lambda_{ex}$ (nm) | $E_{SSET}$ | $k_s$ of donor (s⁻¹) | $k_{SSET}$(s⁻¹) | $k_{SSET}$(s⁻¹) (Average) | $R_0$ (A) | $R$(A) | $R_{model}$(A) (Average) | $E_{TTET}$ | $k_{TTET}$ (s⁻¹) |
|---|---|---|---|---|---|---|---|---|---|---|

2B

TABLE 2

Biocompatible, endogenous fluorophore emitters.

| Endogenous Fluorophores | Excitation Max. (nm) | Emission Max. (nm) |
|---|---|---|
| Amino acids: | | |
| Tryptophan | 280 | 350 |
| Tyrosine | 275 | 300 |
| Phenylalanine | 260 | 280 |
| Structural Proteins: | | |
| Collagen | 325, 360 | 400, 405 |
| Elastin | 290, 325 | 340, 400 |
| Enzymes and Coenzymes: | | |
| flavin adenine dinucleotide | 450 | 535 |
| reduced nicotinamide dinucelotide | 290, 351 | 440, 460 |
| reduced nicotinamide dinucelotide phosphate | 336 | 464 |
| Vitamins: | | |
| Vitamins A | 327 | 510 |
| Vitamins K | 335 | 480 |
| Vitamins D | 390 | 480 |
| Vitamins $B_6$ compounds: | | |
| Pyridoxine | 332, 340 | 400 |
| Pyridoxamine | 335 | 400 |
| Pyridoxal | 330 | 385 |
| Pyridoxic acid | 315 | 425 |
| Pyridoxal phosphate | 5'-330 | 400 |
| Vitamin $B_{12}$ | 275 | 305 |
| Lipids: | | |
| Phospholipids | 436 | 540, 560 |
| Lipofuscin | 340-395 | 540, 430-460 |
| Ceroid | 340-395 | 430-460, 540 |
| Porphyrins | 400-450 | 630, 690 |

FIG. 1 provides an exemplary electromagnetic spectrum in meters (1 nm equals meters).

The nature of the predetermined cellular change will depend on the desired pharmaceutical outcome. Exemplary cellular changes may include, but are not limited to, apoptosis, necrosis, up-regulation of certain genes, down-regulation of certain genes, secretion of cytokines, alteration of cytokine receptor responses, or a combination thereof.

As used herein, an "energy modulation agent" refers to an agent that is capable of receiving an energy input from a source and then re-emitting a different energy to a receiving target. Energy transfer among molecules may occur in a number of ways. The form of energy may be electronic, thermal, electromagnetic, kinetic, or chemical in nature. Energy may be transferred from one molecule to another (intermolecular transfer) or from one part of a molecule to another part of the same molecule (intramolecular transfer). For example, a modulation agent may receive electromagnetic energy and re-emit the energy in the form of thermal energy. In preferred embodiments, the energy modulation agent receives higher energy (e.g. x-ray) and re-emits in lower energy (e.g. UV-A). Some modulation agents may have a very short energy retention time (on the order of fs, e.g. fluorescent molecules) whereas others may have a very long half-life (on the order of minutes to hours, e.g. luminescent or phosphorescent molecules). Suitable energy modulation agents include, but are not limited to, a biocompatible fluorescing metal nanoparticle, fluorescing dye molecule, gold nanoparticle, a water soluble quantum dot encapsulated by polyamidoamine dendrimers, a luciferase, a biocompatible phosphorescent molecule, a combined electromagnetic energy harvester molecule, and a lanthanide chelate capable of intense luminescence. Various exemplary uses of these are described below in preferred embodiments.

The modulation agents may further be coupled to a carrier for cellular targeting purposes. For example, a biocompatible molecule, such as a fluorescing metal nanoparticle or fluorescing dye molecule that emits in the UV-A band, may be selected as the energy modulation agent.

The energy modulation agent may be preferably directed to the desired site (e.g. a tumor) by systemic administration to a subject. For example, a UV-A emitting energy modulation agent may be concentrated in the tumor site by physical insertion or by conjugating the UV-A emitting energy modulation agent with a tumor specific carrier, such as a lipid, chitin or chitin-derivative, a chelate or other functionalized carrier that is capable of concentrating the UV-A emitting source in a specific target tumor.

Additionally, the energy modulation agent can be used alone or as a series of two or more energy modulation agents wherein the energy modulation agents provide an energy cascade. Thus, the first energy modulation agent in the cascade will absorb the activation energy, convert it to a different energy which is then absorbed by the second energy modulation in the cascade, and so forth until the end of the cascade is reached with the final energy modulation agent in the cascade emitting the energy necessary to activate the activatable pharmaceutical agent.

Although the activatable pharmaceutical agent and the energy modulation agent can be distinct and separate, it will be understood that the two agents need not be independent and separate entities. In fact, the two agents may be associated with each other via a number of different configurations. Where the two agents are independent and separately movable from each other, they generally interact with each other via diffusion and chance encounters within a common surrounding medium. Where the activatable pharmaceutical agent and the energy modulation agent are not separate, they may be combined into one single entity.

The initiation energy source can be any energy source capable of providing energy at a level sufficient to activate the activatable agent directly, or to provide the energy modulation agent with the input needed to emit the activation energy for the activatable agent (indirect activation). Preferable initiation energy sources include, but are not limited to, UV-A lamps or fiber optic lines, a light needle, an endoscope, and a linear accelerator that generates x-ray, gamma-ray, or electron beams. In a preferred embodiment the initiation energy capable of penetrating completely through the subject. Within the context of the present invention, the phrase "capable of penetrating completely through the subject" is used to refer to energy that can penetrate to any depth within the subject to activate the activatable pharmaceutical agent. It is not required that the any of the energy applied actually pass completely through the subject, merely that it be capable of doing so in order to permit penetration to any desired depth to activate the activatable pharmaceutical agent. Exemplary initiation energy sources that are capable of penetrating completely through the subject include, but are not limited to, x-rays, gamma rays, electron beams, microwaves and radio waves.

In one embodiment, the source of the initiation energy can be a radiowave emitting nanotube, such as those described by K. Jensen, J. Weldon, H. Garcia, and A. Zettl in the Department of Physics at the University of California at Berkeley (see http://socrates.berkeley.edu/~argon/nanoradio/radio.html, the entire contents of which are hereby incorporated by reference). These nanotubes can be administered to the subject, and preferably would be coupled to the activatable pharmaceutical agent or the energy modulation agent, or both, such that upon application of the initiation energy, the nanotubes would accept the initiation energy (preferably radiowaves), then emit radiowaves in close proximity to the activatable pharmaceutical agent, or in close proximity to the energy modulation agent, to then cause activation of the activatable pharmaceutical agent. In such an embodiment, the nanotubes would act essentially as a radiowave focusing or amplification device in close proximity to the activatable pharmaceutical agent or energy modulation agent.

Alternatively, the energy emitting source may be an energy modulation agent that emits energy in a form suitable for absorption by the transfer agent. For example, the initiation energy source may be acoustic energy and one energy modulation agent may be capable of receiving acoustic energy and emitting photonic energy (e.g. sonoluminescent molecules) to be received by another energy modulation agent that is capable of receiving photonic energy. Other examples include transfer agents that receive energy at x-ray wavelength and emit energy at UV wavelength, preferably at UV-A wavelength. As noted above, a plurality of such energy modulation agents may be used to form a cascade to transfer energy from initiation energy source via a series of energy modulation agents to activate the activatable agent.

Signal transduction schemes as a drug delivery vehicle may be advantageously developed by careful modeling of the cascade events coupled with metabolic pathway knowledge to sequentially or simultaneously activate multiple activatable pharmaceutical agents to achieve multiple-point alterations in cellular function.

Photoactivatable agents may be stimulated by an energy source, such as irradiation, resonance energy transfer, exciton migration, electron injection, or chemical reaction, to an activated energy state that is capable of effecting the predetermined cellular change desired. In a preferred embodiment, the photoactivatable agent, upon activation, binds to DNA or RNA or other structures in a cell. The activated energy state of the agent is capable of causing damage to cells, inducing apoptosis. The mechanism of apoptosis is associated with an enhanced immune response that reduces the growth rate of cell proliferation disorders and may shrink solid tumors, depending on the state of the patient's immune system, concentration of the agent in the tumor, sensitivity of the agent to stimulation, and length of stimulation.

A preferred method of treating a cell proliferation disorder of the present invention administers a photoactivatable agent to a patient, stimulates the photoactivatable agent to induce cell damage, and generates an auto vaccine effect. In one further preferred embodiment, the photoactivatable agent is stimulated via a resonance energy transfer.

One advantage is that multiple wavelengths of emitted radiation may be used to selectively stimulate one or more photoactivatable agents or energy modulation agents capable of stimulating the one or more photoactivatable agents. The energy modulation agent is preferably stimulated at a wavelength and energy that causes little or no damage to healthy cells, with the energy from one or more energy modulation agents being transferred, such as by Foerster Resonance Energy Transfer, to the photoactivatable agents that damage the cell and cause the onset of the desired cellular change, such as apoptosis of the cells.

Another advantage is that side effects can be greatly reduced by limiting the production of free radicals, singlet oxygen, hydroxides and other highly reactive groups that are known to damage healthy cells. Furthermore, additional additives, such as antioxidants, may be used to further reduce undesired effects of irradiation.

Resonance Energy Transfer (RET) is an energy transfer mechanism between two molecules having overlapping emission and absorption bands. Electromagnetic emitters are capable of converting an arriving wavelength to a longer wavelength. For example, UV-B energy absorbed by a first molecule may be transferred by a dipole-dipole interaction to a UV-A-emitting molecule in close proximity to the UV-B-absorbing molecule. Alternatively, a material absorbing a shorter wavelength may be chosen to provide RET to a non-emitting molecule that has an overlapping absorption band with the transferring molecule's emission band. Alternatively, phosphorescence, chemiluminescence, or bioluminescence may be used to transfer energy to a photoactivatable molecule.

Alternatively, one can administer the initiation energy source to the subject. Within the context of the present invention, the administering of the initiation energy source means the administration of an agent, that itself produces the initiation energy, in a manner that permits the agent to arrive at the target cell within the subject without being surgically inserted into the subject. The administration can take any form, including, but not limited to, oral, intravenous, intraperitoneal, inhalation, etc. Further, the initiation energy source in this embodiment can be in any form, including, but not limited to, tablet, powder, liquid solution, liquid suspension, liquid dispersion, gas or vapor, etc. In this embodiment, the initiation energy source includes, but is not limited to, chemical energy sources, nanoemitters, nanochips, and other nanomachines that produce and emit energy of a desired frequency. Recent advances in nanotechnology have provided examples of various devices that are nanoscale and produce or emit energy, such as the Molecular Switch (or Mol-Switch) work by Dr. Keith Firman of the EC Research and Development Project, or the work of Cornell et al. (1997) who describe the construction of nanomachines based around ion-channel switches only 1.5 nm in size, which use ion channels formed in an artificial membrane by two gramicidin molecules: one in the lower layer of the membrane attached to a gold electrode and one in the upper layer tethered to biological receptors such as antibodies or nucleotides. When the receptor captures a target molecule or cell, the ion channel is broken, its conductivity drops, and the biochemical signal is converted into an electrical signal. These nanodevices could also be coupled with the present invention to provide targeting of the target cell, to deliver the initiation energy source directly at the desired site. In another embodiment, the present invention includes the administration of the activatable pharmaceutical agent, along with administration of a source of chemical energy such as chemiluminescence, phosphorescence or bioluminescence. The source of chemical energy can be a chemical reaction between two or more compounds, or can be induced by activating a chemiluminescent, phosphorescent or bioluminescent compound with an appropriate activation energy, either outside the subject or inside the subject, with the chemiluminescence, phosphorescence or bioluminescence being allowed to activate the activatable pharmaceutical agent in vivo after administration. The administration of the activatable pharmaceutical agent and the source of chemical energy can be performed sequentially in any order or can be performed simultaneously. In the case of certain sources of such chemical energy, the administration of the chemical energy source can be performed after activation outside the subject, with the lifetime of the emission of the energy being up to several hours for certain types of phosphorescent materials for example. There are no known previous efforts to use resonance energy transfer of any kind to activate an intercalator to bind DNA.

Yet another example is that nanoparticles or nanoclusters of certain atoms may be introduced such that are capable of resonance energy transfer over comparatively large distances, such as greater than one nanometer, more preferably greater than five nanometers, even more preferably at least 10 nanometers. Functionally, resonance energy transfer may have a large enough "Foerster" distance ($R_0$), such that nanoparticles in one part of a cell are capable of stimulating activation of photoactivatable agents disposed in a distant portion of the cell, so long as the distance does not greatly exceed $R_0$. For example, gold nanospheres having a size of 5 atoms of gold have been shown to have an emission band in the ultraviolet range, recently.

The present invention treatment may also be used for inducing an auto vaccine effect for malignant cells, including those in solid tumors. To the extent that any rapidly dividing cells or stem cells may be damaged by a systemic treatment, then it may be preferable to direct the stimulating energy directly toward the tumor, preventing damage to most normal, healthy cells or stem cells by avoiding photoactivation or resonant energy transfer of the photoactivatable agent.

Alternatively, a treatment may be applied that slows or pauses mitosis. Such a treatment is capable of slowing the division of rapidly dividing healthy cells or stem cells during the treatment, without pausing mitosis of cancerous cells. Alternatively, a blocking agent is administered preferentially to malignant cells prior to administering the treatment that slows mitosis.

In one embodiment, an aggressive cell proliferation disorder has a much higher rate of mitosis, which leads to selective destruction of a disproportionate share of the malignant cells during even a systemically administered treatment. Stem cells and healthy cells may be spared from wholesale programmed cell death, even if exposed to photoactivated agents, provided that such photoactivated agents degenerate from the excited state to a lower energy state prior to binding, mitosis or other mechanisms for creating damage to the cells of a substantial fraction of the healthy stem cells. Thus, an auto-immune response may not be induced.

Alternatively, a blocking agent may be used that prevents or reduces damage to stem cells or healthy cells, selectively, which would otherwise be impaired. The blocking agent is selected or is administered such that the blocking agent does not impart a similar benefit to malignant cells, for example.

In one embodiment, stem cells are targeted, specifically, for destruction with the intention of replacing the stem cells with a donor cell line or previously stored, healthy cells of the patient. In this case, no blocking agent is used. Instead, a carrier or photosensitizer is used that specifically targets the stem cells.

Any of the photoactivatable agents may be exposed to an excitation energy source implanted in a tumor. The photoactive agent may be directed to a receptor site by a carrier having a strong affinity for the receptor site. Within the context of the present invention, a "strong affinity" is preferably an affinity having an equilibrium dissociation constant, $K_i$, at least in the nanomolar, nM, range or higher. Preferably, the carrier may be a polypeptide and may form a covalent bond with a photoactive agent, for example. The polypeptide may be an insulin, interleukin, thymopoietin or transferrin, for example. Alternatively, a photoactive agent may have a strong affinity for the target cell without binding to a carrier.

A receptor site may be any of the following: nucleic acids of nucleated blood cells, molecule receptor sites of nucleated blood cells, the antigenic sites on nucleated blood cells, epitopes, or other sites where photoactive agents are capable of destroying a targeted cell.

In one embodiment, thin fiber optic lines are inserted in the tumor and laser light is used to photoactivate the agents. In another embodiment, a plurality of sources for supplying electromagnetic radiation energy or energy transfer are provided by one or more molecules administered to a patient. The molecules may emit stimulating radiation in the correct band of wavelength to stimulate the photoactivatable agents, or the molecules may transfer energy by a resonance energy transfer or other mechanism directly to the photoactivatable agent or indirectly by a cascade effect via other molecular interactions.

In another embodiment, the patient's own cells are removed and genetically modified to provide photonic emissions. For example, tumor or healthy cells may be removed, genetically modified to induce bioluminescence and may be reinserted at the site of the tumor to be treated. The modified, bioluminescent cells may be further modified to prevent further division of the cells or division of the cells only so long as a regulating agent is present. Administration of an intercalator, systemically or targeting tumor cells, that is capable of photoactivation by bioluminescent cells may produce conditions suitable for creating an auto vaccine effect due to apoptosis of malignant cells. Preferably, apoptosis triggers and stimulates the body to develop an immune response targeting the malignant cells.

In a further embodiment, a biocompatible emitting source, such as a fluorescing metal nanoparticle or fluorescing dye molecule, is selected that emits in the UV-A band. The UV-A emitting source is directed to the site of a tumor. The UV-A emitting source may be directed to the site of the tumor by systemically administering the UV-A emitting source. Preferably, the UV-A emitting source is concentrated in the tumor site, such as by physical insertion or by conjugating the UV-A emitting molecule with a tumor specific carrier, such as a lipid, chitin or chitin-derivative, a chelate or other functionalized carrier that is capable of concentrating the UV-A emitting source in a specific target tumor, as is known in the art.

In one preferred embodiment, the UV-A emitting source is a gold nanoparticle comprising a cluster of 5 gold atoms, such as a water soluble quantum dot encapsulated by polyamidoamine dendrimers. The gold atom clusters may be produced through a slow reduction of gold salts (e.g. $HAuCl_4$ or $AuBr_3$) or other encapsulating amines, for example. One advantage of such a gold nanoparticle is the increased Foerster distance (i.e. $R_0$), which may be greater than 100 angstroms. The equation for determining the Foerster distance is substantially different from that for molecular fluorescence, which is limited to use at distances less than 100 angstroms. It is believed that the gold nanoparticles are governed by nanoparticle surface to dipole equations with a $1/R^4$ distance dependence rather than a $1/R^6$ distance dependence. For example, this permits cytoplasmic to nuclear energy transfer between metal nanoparticles and a photoactivatable molecule, such as a psoralen and more preferably an 8-methoxypsoralen (8-MOP) administered orally to a patient, which is known to be safe and effective at inducing an apoptosis of leukocytes.

In another embodiment, a UV- or light-emitting luciferase is selected as the emitting source for exciting a photoactivatable agent. A luciferase may be combined with ATP or another molecule, which may then be oxygenated with additional molecules to stimulate light emission at a desired wavelength. Alternatively, a phosphorescent emitting source may be used. One advantage of a phosphorescent emitting source is that the phosphorescent emitting molecules or other source may be electroactivated or photoactivated prior to insertion into the tumor either by systemic administration or direct insertion into the region of the tumor. Phosphorescent materials may have longer relaxation times than fluorescent materials, because relaxation of a triplet state is subject to forbidden energy state transitions, storing the energy in the excited triplet state with only a limited number of quantum mechanical energy transfer processes available for returning to the lower energy state. Energy emission is delayed or prolonged from a fraction of a second to several hours. Otherwise, the energy emitted during phosphorescent relaxation is not otherwise different than fluorescence, and the range of wavelengths may be selected by choosing a particular phosphor.

In another embodiment, a combined electromagnetic energy harvester molecule is designed, such as the combined light harvester disclosed in J. Am. Chem. Soc. 2005, 127, 9760-9768, the entire contents of which are hereby incorporated by reference. By combining a group of fluorescent molecules in a molecular structure, a resonance energy transfer cascade may be used to harvest a wide band of electromagnetic radiation resulting in emission of a narrow band of fluorescent energy. By pairing a combined energy harvester with a photoactivatable molecule, a further energy resonance transfer excites the photoactivatable molecule, when the photoactivatable molecule is nearby stimulated combined energy harvester molecules. Another example of a harvester molecule is disclosed in FIG. 4 of "Singlet-Singlet and Triplet-Triplet Energy Transfer in Bichromophoric Cyclic Peptides," M.S. Thesis by M. O. Guler, Worcester Polytechnic Institute, May 18, 2002, which is incorporated herein by reference.

In another embodiment, a Stokes shift of an emitting source or a series of emitting sources arranged in a cascade is selected to convert a shorter wavelength energy, such as X-rays, to a longer wavelength fluorescence emission such a optical or UV-A, which is used to stimulate a photoactivatable molecule at the location of the tumor cells. Preferably, the photoactivatable molecule is selected to cause an apoptosis sequence in tumor cells without causing substantial harm to normal, healthy cells. More preferably, the apoptosis sequence then leads to an auto vaccine effect that targets the malignant tumor cells throughout the patient's body.

In an additional embodiment, the photoactivatable agent can be a photocaged complex having an active agent (which can be a cytotoxic agent or can be an activatable pharmaceutical agent) contained within a photocage. The active agent is bulked up with other molecules that prevent it from binding to specific targets, thus masking its activity. When the photocage complex is photoactivated, the bulk falls off, exposing the active agent. In such a photocage complex, the photocage molecules can be photoactive (i.e. when photoactivated, they are caused to dissociate from the photocage complex, thus exposing the active agent within), or the active agent can be the photoactivatable agent (which when photoactivated causes the photocage to fall off), or both the photocage and the active agent are photoactivated, with the same or different wavelengths. For example, a toxic chemotherapeutic agent can be photocaged, which will reduce the systemic toxicity when delivered. Once the agent is concentrated in the tumor, the agent is irradiated with an activation energy. This causes the "cage" to fall off, leaving a cytotoxic agent in the tumor cell. Suitable photocages include those disclosed by Young and Deiters in "Photochemical Control of Biological Processes", *Org. Biomol. Chem.*, 5, pp. 999-1005 (2007) and "Photochemical Hammerhead Ribozyme Activation", *Bioorganic & Medicinal Chemistry Letters*, 16 (10), pp. 2658-2661 (2006), the contents of which are hereby incorporated by reference.

In a further embodiment, some of the tumor cells are treated in vitro using a UV-A source to stimulate 8-MOP. Apoptosis of the tumor cells is monitored, and some or all of the fragments and remnants of the apoptosis process are reintroduced into the site of a tumor. Preferably, the portion of fragments, cellular structures and remnants are selected such that an auto vaccine effect is generated that leads to further apoptosis of tumor cells without substantially harming healthy tissues, causing solid tumors to shrink.

In one embodiment, a lanthanide chelate capable of intense luminescence is used. For example, a lanthanide chelator may be covalently joined to a coumarin or coumarin derivative or a quinolone or quinolone-derivative sensitizer. Sensitizers may be a 2- or 4-quinolone, a 2- or 4-coumarin, or derivatives or combinations of these examples. A carbostyril 124 (7-amino-4-methyl-2-quinolone), a coumarin 120 (7-amino-4-methyl-2-coumarin), a coumarin 124 (7-amino-4-(trifluoromethyl)-2-coumarin), aminoinethyltrimethylpsoralen or other similar sensitizer may be used. Chelates may be selected to form high affinity complexes with lanthanides, such as terbium or europium, through chelator groups, such as DTPA. Such chelates may be coupled to any of a wide variety of well known probes or carriers, and may be used for resonance energy transfer to a psoralen or psoralen-derivative, such as 8-MOP, or other photoactive molecules capable of binding DNA and causing the initiation of an apoptosis process of rapidly dividing cancer cells. In this way, the treatment may be targeted to especially aggressive forms of cell proliferation disorders that are not successfully treated by conventional chemotherapy, radiation or surgical techniques. In one alternative example, the lanthanide chelate is localized at the site of the tumor using an appropriate carrier molecule, particle or polymer, and a source of electromagnetic energy is introduced by minimally invasive procedures to irradiate the tumor cells, after exposure to the lanthanide chelate and a photoactive molecule.

In another embodiment, a biocompatible, endogenous fluorophore emitter is selected to stimulate resonance energy transfer to a photoactivatable molecule. A biocompatible emitter with an emission maxima within the absorption range of the biocompatible, endogenous fluorophore emitter may be selected to stimulate an excited state in fluorophore emitter. One or more halogen atoms may be added to any cyclic ring structure capable of intercalation between the stacked nucleotide bases in a nucleic acid (either DNA or RNA) to confer new photoactive properties to the intercalator. Any intercalating molecule (psoralens, coumarins, or other polycyclic ring structures) may be selectively modified by halogenation or addition of non-hydrogen bonding ionic substituents to impart advantages in its reaction photochemistry and its competitive binding affinity for nucleic acids over cell membranes or charged proteins, as is known in the art.

Recently, photosensitizers have been developed for treating cell proliferation disorders using photodynamic therapy. Table 3 provides an assortment of known photosensitizers that are useful in treating cell proliferation disorders.

TABLE 3

Photosensitizers for cell proliferation disorders.

| Photo-sensitizer | Dose | Drug-light interval | Wavelength of activation | Length of photo-sensitization |
|---|---|---|---|---|
| Photofrin (II) | 2 mg/kg | 48 hrs | 630 nm | 4-6 weeks |
| Foscan | 0.1 mg/kg | 4-6 days | 652 nm | 2 weeks |
| Lutetium texahyrin | 2-6 mg/kg | 3 to 24 hrs | 732 nm | 24-48 hrs |

Skin photosensitivity is a major toxicity of the photosensitizers. Severe sunburn occurs if skin is exposed to direct sunlight for even a few minutes. Early murine research hinted at a vigorous and long term stimulation of immune response; however, actual clinical testing has failed to achieve the early promises of photodynamic therapies. The early photosensitizers for photodynamic therapies targeted type II responses, which created singlet oxygen when photoactivated in the presence of oxygen. The singlet oxygen caused cellular necrosis and was associated with inflammation and an immune response. However, tumors are now known to down regulate the immune response over time, and it is thought that this is one of the reasons that clinical results are not as dramatic as promised by the early murine research. Some additional photosensitizers have been developed to induce type I responses, directly damaging cellular structures, which result in apoptosis of tumor cells.

Porfimer sodium (Photofrin; QLT Therapeutics, Vancouver, BC, Canada), is a partially purified preparation of hematoporphyrin derivative (HpD). Photofrin has been approved by the US Food and Drug Administration for the treatment of obstructing esophageal cancer, microinvasive endobronchial non-small cell lung cancer, and obstructing endobronchial non-small cell lung cancer. Photofrin is activated with 630 nm, which has a tissue penetration of approximately 2 to 5 mm. Photofrin has a relatively long duration of skin photosensitivity (approximately 4 to 6 weeks).

Tetra (m-hydroxyphenyl) chlorin (Foscan; Scotia Pharmaceuticals, Stirling, UK), is a synthetic chlorin compound that is activated by 652 nm light. Clinical studies have demonstrated a tissue effect of up to 10 mm with Foscan and 652 nm light. Foscan is more selectively a photosensitizer in tumors than normal tissues, and requires a comparatively short light activation time. A recommended dose of 0.1 mg/kg is comparatively low and comparatively low doses of light may be used. Nevertheless, duration of skin photosensitivity is reasonable (approximately 2 weeks). However, Foscan induces a comparatively high yield of singlet oxygen, which may be the primary mechanism of DNA damage for this molecule.

Figure 2A:
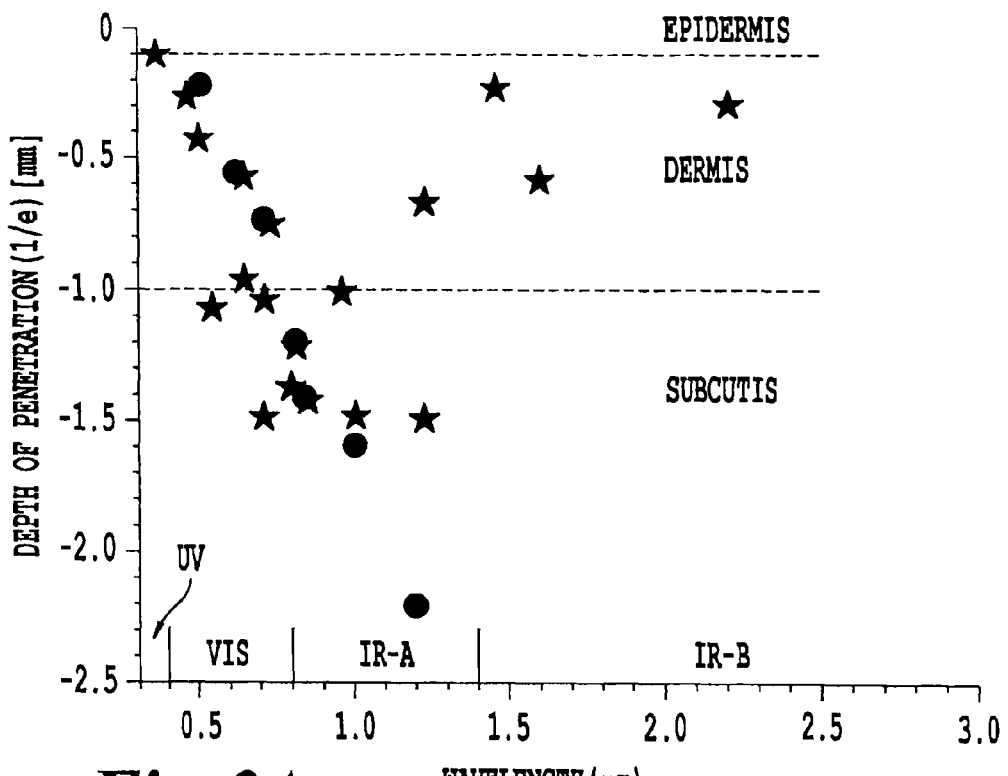
FIG. 2A and FIG. 2B are graphical representations of the depth of penetration of various wavelengths of energy into living tissue.
Figure 2B:
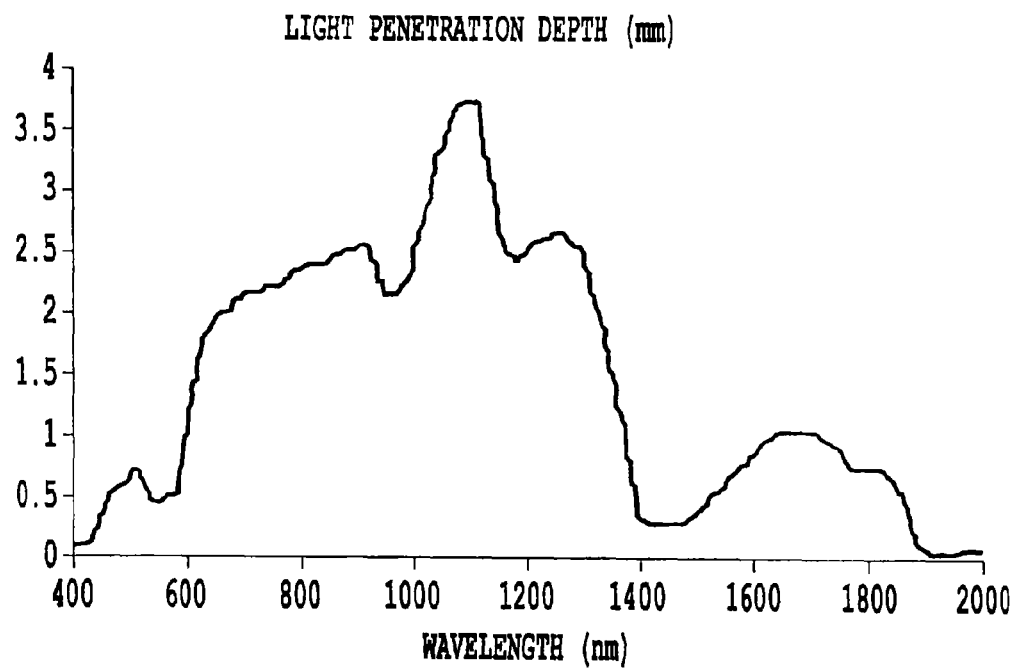

Motexafin lutetium (Lutetium texaphryin) is activated by light in the near infrared region (732 nm). Absorption at this wavelength has the advantage of potentially deeper penetration into tissues, compared with the amount of light used to activate other photosensitizers (FIGS. 2A and 2B). Lutetium texaphyrin also has one of the greatest reported selectivities for tumors compared to selectivities of normal tissues. Young S W, et al.: Lutetium texaphyrin (PCI-0123) a near-infrared, water-soluble photosensitizer. Photochem Photobiol 1996, 63:892-897. In addition, its clinical use is associated with a shorter duration of skin photosensitivity (24 to 48 hours). Lutetium texaphyrin has been evaluated for metastatic skin cancers. It is currently under investigation for treatment of recurrent breast cancer and for locally recurrent prostate cancer. The high selectivity for tumors promises improved results in clinical trials.

In general, the approach may be used with any source for the excitation of higher electronic energy states, such as electrical, chemical and/or radiation, individually or combined into a system for activating an activatable molecule. The process may be a photophoresis process or may be similar to photophoresis. While photophoresis is generally thought to be limited to photonic excitation, such as by UV-light, other forms of radiation may be used as a part of a system to activate an activatable molecule. Radiation includes ionizing radiation which is high energy radiation, such as an X-ray or a gamma ray, which interacts to produce ion pairs in matter. Radiation also includes high linear energy transfer irradiation, low linear energy transfer irradiation, alpha rays, beta rays, neutron beams, accelerated electron beams, and ultraviolet rays. Radiation also includes proton, photon and fission-spectrum neutrons. Higher energy ionizing radiation may be combined with chemical processes to produce energy states favorable for resonance energy transfer, for example. Other combinations and variations of these sources of excitation energy may be combined as is known in the art, in order to stimulate the activation of an activatable molecule, such as 8-MOP. In one example, ionizing radiation is directed at a solid tumor and stimulates, directly or indirectly, activation of 8-MOP, as well as directly damaging the DNA of malignant tumor cells. In this example, either the effect of ionizing radiation or the photophoresis-like activation of 8-MOP may be thought of as an adjuvant therapy to the other.

In one embodiment, the present invention provides a method for treating a cell proliferation disorder in a subject, comprising:
  (1) administering to the subject an activatable pharmaceutical agent that is capable of effecting a predetermined cellular change when activated; and
  (2) applying an initiation energy from an initiation energy source to the subject, wherein the initiation energy source is a source of energy capable of penetrating completely through the subject, and wherein the applying activates the activatable agent in situ,
  thus causing the predetermined cellular change to occur, wherein occurrence of the predetermined cellular change causes an increase in rate or decrease in rate of cell proliferation to treat the cell proliferation disorder.

In a further embodiment, the present invention provides a method for treating a cell proliferation disorder in a subject, comprising:
  (1) administering to the subject one or more energy modulation agents and an activatable pharmaceutical agent that is capable of effecting a predetermined cellular change when activated; and
  (2) applying an initiation energy from an initiation energy source to the subject,
  wherein the one or more energy modulation agents convert the initiation energy applied to UV-A or visible energy, which then activates the activatable agent in situ,
  thus causing the predetermined cellular change to occur, wherein occurrence of the predetermined cellular change causes an increase in rate or decrease in rate of cell proliferation to treat the cell proliferation disorder.

In a further embodiment, the present invention provides a method for treating a cell proliferation disorder in a subject, comprising:
  (1) administering to the subject an activatable pharmaceutical agent that is capable of effecting a predetermined cellular change when activated; and
  (2) applying an initiation energy from an initiation energy source to the subject,
  wherein the initiation energy applied and activatable pharmaceutical agent upon activation produce insufficient singlet oxygen in the subject to produce cell lysis, and wherein the initiation energy activates the activatable pharmaceutical agent in situ,
  thus causing the predetermined cellular change to occur, wherein occurrence of the predetermined cellular change causes an increase in rate or decrease in rate of cell proliferation to treat the cell proliferation disorder.

Work in the area of photodynamic therapy has shown that the amount of singlet oxygen required to cause cell lysis, and thus cell death, is $0.32 \times 10^{-3}$ mol/liter or more, or $10^9$ singlet oxygen molecules/cell or more. However, in the present invention, it is most preferable to avoid production of an amount of singlet oxygen that would cause cell lysis, due to its indiscriminate nature of attack, lysing both target cells and healthy cells. Accordingly, it is most preferred in the present invention that the level of singlet oxygen production caused by the initiation energy used or activatable pharmaceutical agent upon activation be less than level needed to cause cell lysis.

In yet another embodiment, the activatable pharmaceutical agent, preferably a photoactive agent, is directed to a receptor site by a carrier having a strong affinity for the receptor site. The carrier may be a polypeptide and may form a covalent bond with a photo active agent, for example. The polypeptide may be an insulin, interleukin, thymopoietin or transferrin, for example. Alternatively, a photoactive pharmaceutical agent may have a strong affinity for the target cell without a binding to a carrier.

For example, a treatment may be applied that acts to slow or pause mitosis. Such a treatment is capable of slowing the division of rapidly dividing healthy cells or stem cells without pausing mitosis of cancerous cells. Thus, the difference in growth rate between the non-target cells and target cells are further differentiated to enhance the effectiveness of the methods of the present invention.

In another example, an aggressive cell proliferation disorder has a much higher rate of mitosis, which leads to selective destruction of a disproportionate share of the malignant cells during even a systemically administered treatment. Stem cells and healthy cells may be spared from wholesale programmed cell death even if exposed to photoactivated agents that cause apoptosis, provided that such photoactivated agents degenerate from the excited state to a lower energy state prior to binding, mitosis or other mechanisms for creating damage to the cells of a substantial fraction of the healthy stem cells. To further protect healthy cells from the effect of photoactivatable agents, blocking agents that block uptake of the photoactivatable agents, prior to their activation, may be administered.

U.S. Pat. No. 6,235,508, discloses that a variety of blocking agents have been found to be suitable for this purpose, some of which are traditional antioxidants, and some of which are not. Suitable blocking agents include, but are not limited to, histidine, cysteine, tryrosine, tryptophan, ascorbate, N-acetyl cysteine, propyl gallate, mercaptopropionyl glycine, butylated hydroxytoluene (BHT) and butylated hydroxyanisole (BHA).

In a further embodiment, methods in accordance with the present invention may further include adding an additive to alleviate treatment side-effects. Exemplary additives may include, but are not limited to, antioxidants, adjuvant, or combinations thereof. In one exemplary embodiment, psoralen is used as the activatable pharmaceutical agent, UV-A is used as the activating energy, and antioxidants are added to reduce the unwanted side-effects of irradiation.

The activatable pharmaceutical agent and derivatives thereof as well as the energy modulation agent, can be incorporated into pharmaceutical compositions suitable for administration. Such compositions typically comprise the activatable pharmaceutical agent and a pharmaceutically acceptable carrier. The pharmaceutical composition also comprises at least one additive having a complementary therapeutic or diagnostic effect, wherein the additive is one selected from an antioxidant, an adjuvant, or a combination thereof.

As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the compound of the present invention to affect solubility or clearance of the compound. These molecules may also be synthesized with D-amino acids to increase resistance to enzymatic degradation. If necessary, the activatable pharmaceutical agent can be co-administered with a solubilizing agent, such as cyclodextran.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, rectal administration, and direct injection into the affected area, such as direct injection into a tumor. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

Methods of administering agents according to the present invention are not limited to the conventional means such as injection or oral infusion, but include more advanced and complex forms of energy transfer. For example, genetically engineered cells that carry and express energy modulation agents may be used. Cells from the host may be transfected with genetically engineered vectors that express bioluminescent agents. Transfection may be accomplished via in situ gene therapy techniques such as injection of viral vectors or gene guns, or may be performed ex vivo by removing a sample of the host's cells and then returning to the host upon successful transfection.

Such transfected cells may be inserted or otherwise targeted at the site where diseased cells are located. In this embodiment, the initiation energy source may be a biochemical source as such ATP, in which case the initiation energy source is considered to be directly implanted in the transfected cell. Alternatively, a conventional micro-emitter device capable of acting as an initiation energy source may be transplanted at the site of the diseased cells.

It will also be understood that the order of administering the different agents is not particularly limited. Thus in some embodiments the activatable pharmaceutical agent may be administered before the energy modulation agent, while in other embodiments the energy modulation agent may be administered prior to the activatable pharmaceutical agent. It will be appreciated that different combinations of ordering may be advantageously employed depending on factors such as the absorption rate of the agents, the localization and molecular trafficking properties of the agents, and other pharmacokinetics or pharmacodynamics considerations.

An advantage of the methods of the present invention is that by specifically targeting cells affected by a cell proliferation disorder, such as rapidly dividing cells, and triggering a cellular change, such as apoptosis, in these cells in situ, the immune system of the host may be stimulated to have an immune response against the diseased cells. Once the host's own immune system is stimulated to have such a response, other diseased cells that are not treated by the activatable pharmaceutical agent may be recognized and be destroyed by the host's own immune system. Such autovaccine effects may be obtained, for example, in treatments using psoralen and UV-A.

In another aspect, the present invention also provides methods for producing an autovaccine, including: (1) providing a population of targeted cells; (2) treating the cells ex vivo with a psoralen or a derivative thereof; (3) activating the psoralen with a UV-A source to induce apoptosis in the targeted cells; and (4) returning the apoptic cells back to the host to induce an autovaccine effect against the targeted cell, wherein the apoptic cells cause an autovaccine effect.

A further embodiment is the use of the present invention for the treatment of skin cancer. In this example, a photo-activatable agent, preferably psoralen, is given to the patient, and is delivered to the skin lesion via the blood supply. An activation source having limited penetration ability (such as UV or IR) is shined directly on the skin—in the case of psoralen, it would be a UV light, or an IR source. With the use of an IR source, the irradiation would penetrate deeper and generate UV via two single photon events with psoralen.

In a further embodiment, methods according to this aspect of the present invention further include a step of separating the components of apoptic cells into fractions and testing each fraction for autovaccine effect in a host. The components thus isolated and identified may then serve as an effective autovaccine to stimulate the host's immune system to suppress growth of the targeted cells.

The present invention methods can be used alone or in combination with other therapies for treatment of cell proliferation disorders. Additionally, the present invention methods can be used, if desired, in conjunction with recent advances in chronomedicine, such as that detailed in Giacchetti et al, *Journal of Clinical Oncology*, Vol 24, No 22 (August 1), 2006: pp. 3562-3569. In chronomedicine it has been found that cells suffering from certain types of disorders, such as cancer, respond better at certain times of the day than at others. Thus, chronomedicine could be used in conjunction with the present methods in order to augment the effect of the treatments of the present invention.

In another aspect, the present invention further provides systems and kits for practicing the above described methods.

In one embodiment, a system in accordance with the present invention may include: (1) an initiation energy source; (2) one or more energy modulation agents; and (3) one or more activatable pharmaceutical agents.

In another embodiment, a system in accordance with the present invention may include an initiation energy source and one or more activatable pharmaceutical agents.

Figure 3:
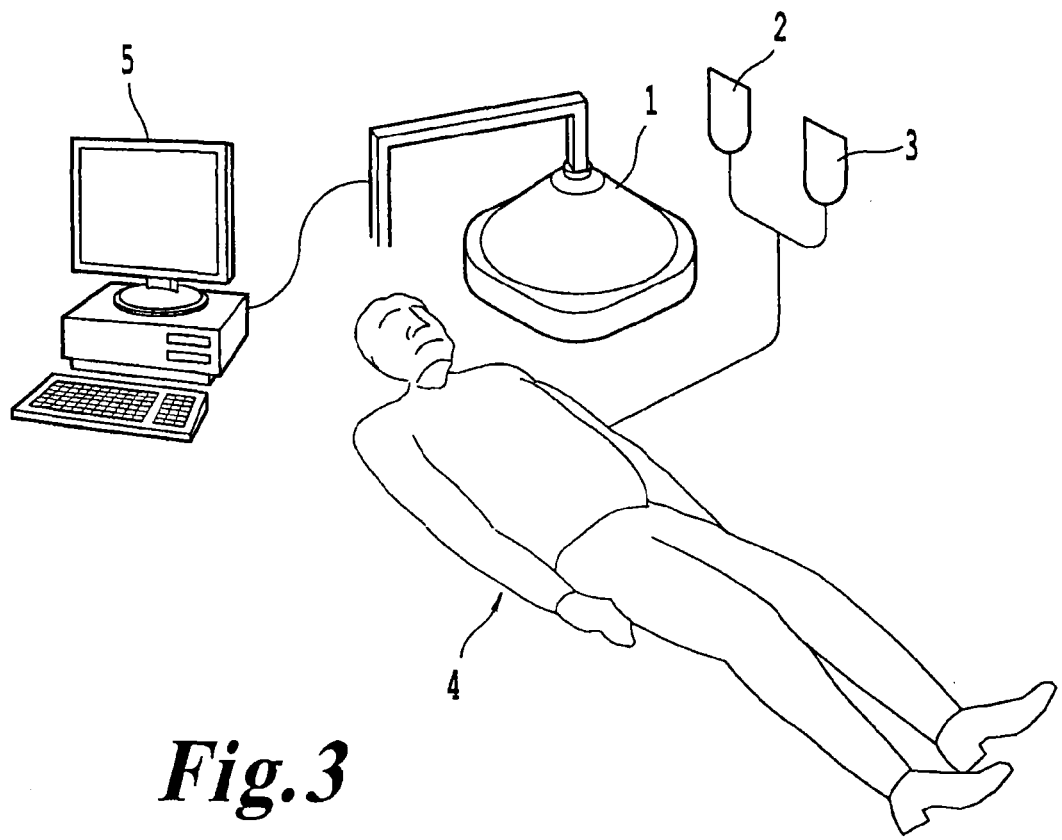
FIG. 3 illustrates a system according to one exemplary embodiment of the present invention.

FIG. 3 illustrates a system according to one exemplary embodiment of the present invention. Referring to FIG. 3, an exemplary system according to one embodiment of the present invention may have an initiation energy source 1 directed at the subject 4. An activatable pharmaceutical agent 2 and an energy modulation agent 3 are administered to the subject 4. The initiation energy source may additionally be controlled by a computer system 5 that is capable of directing the delivery of the initiation energy.

In preferred embodiments, the initiation energy source may be a linear accelerator equipped with image guided computer-control capability to deliver a precisely calibrated beam of radiation to a pre-selected coordinate. One example of such linear accelerators is the SmartBeam™ IMRT (intensity modulated radiation therapy) system from Varian medical systems (Varian Medical Systems, Inc., Palo Alto, Calif.).

In other embodiments, endoscopic or laproscopic devices equipped with appropriate initiation energy emitter may be used as the initiation energy source. In such systems, the initiation energy may be navigated and positioned at the pre-selected coordinate to deliver the desired amount of initiation energy to the site.

In further embodiments, dose calculation and robotic manipulation devices may also be included in the system.

In yet another embodiment, there is also provided a computer implemented system for designing and selecting suitable combinations of initiation energy source, energy transfer agent, and activatable pharmaceutical agent, comprising:

a central processing unit (CPU) having a storage medium on which is provided:
a database of excitable compounds;
a first computation module for identifying and designing an excitable compound that is capable of binding with a target cellular structure or component; and
a second computation module predicting the resonance absorption energy of the excitable compound, wherein the system, upon selection of a target cellular structure or component, computes an excitable compound that is capable of binding with the target structure followed by a computation to predict the resonance absorption energy of the excitable compound.

Figure 4:
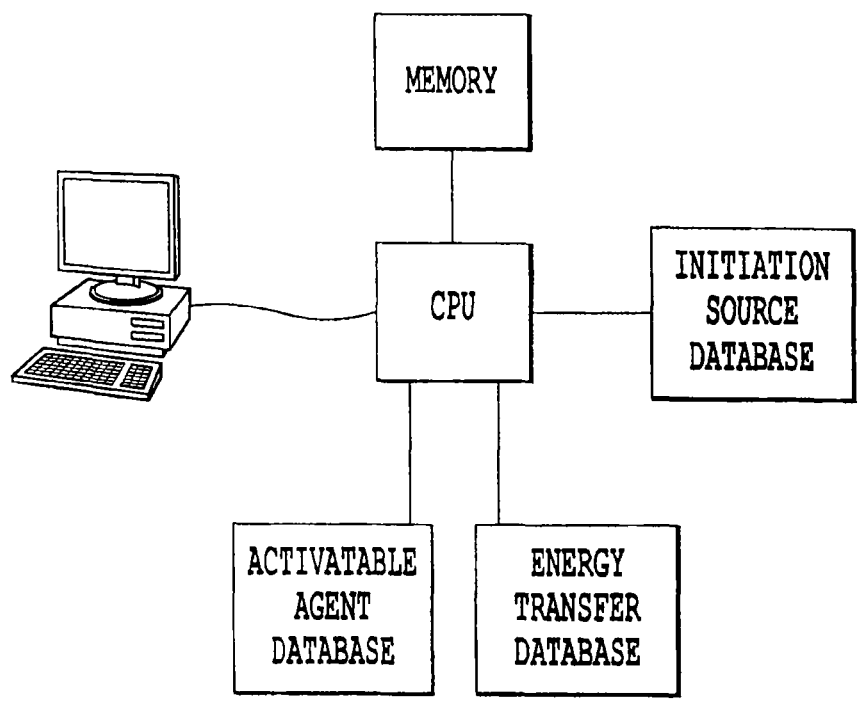
FIG. 4 illustrates an exemplary computer implemented system according to an embodiment of the present invention.

FIG. 4 illustrates an exemplary computer implemented system according to this embodiment of the present invention. Referring to FIG. 4, an exemplary computer-implemented system according to one embodiment of the present invention may have a central processing unit (CPU) connected to a memory unit, configured such that the CPU is capable of processing user inputs and selecting a combination of initiation source, activatable pharmaceutical agent, and energy transfer agent based on an energy spectrum comparison for use in a method of the present invention.

Figure 5:
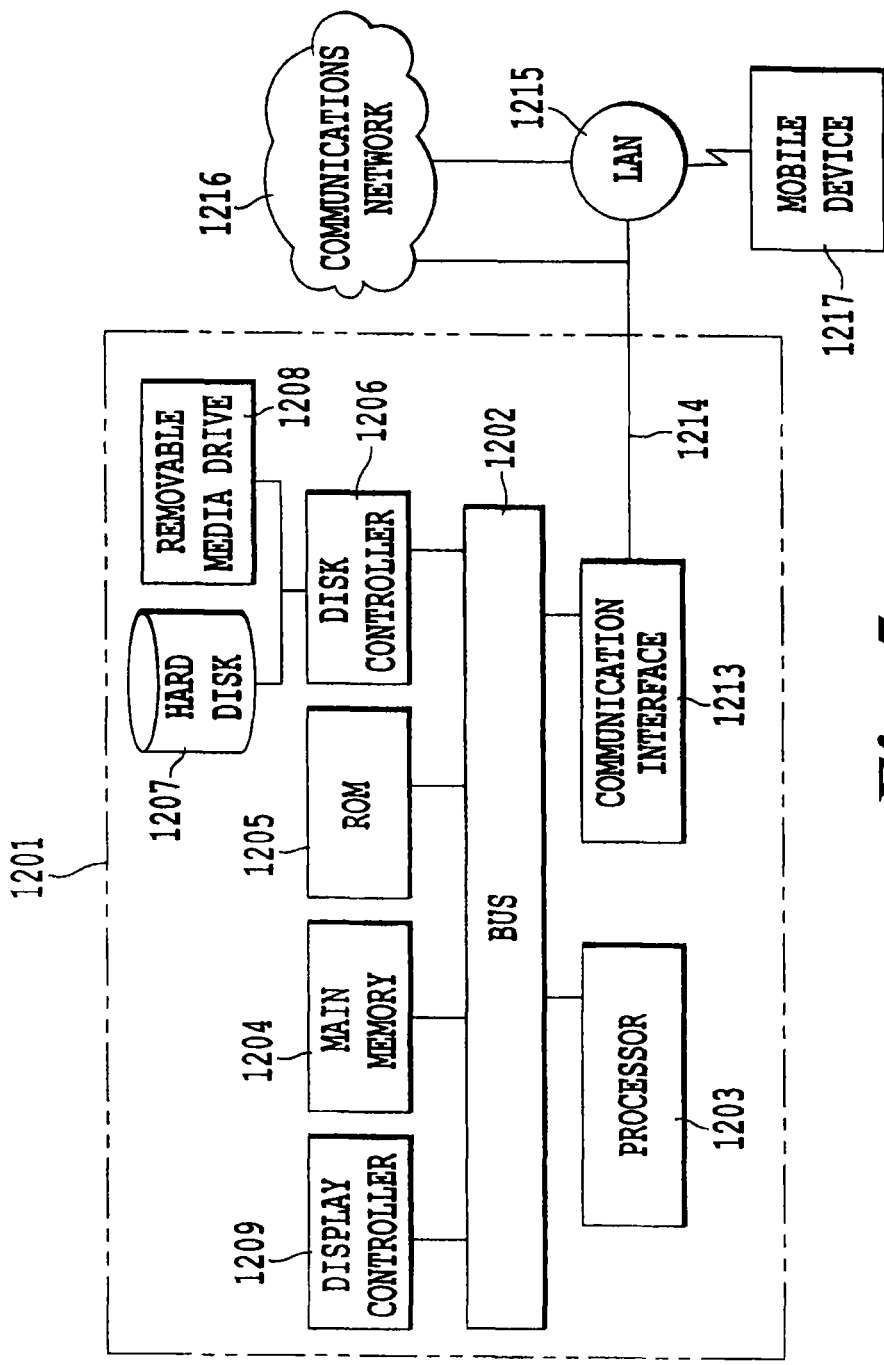
FIG. 5 illustrates an exemplary computer system (1201) for implementing various embodiments of the present invention.

FIG. 5 illustrates a computer system 1201 for implementing various embodiments of the present invention. The computer system 1201 may be used as the controller 55 to perform any or all of the functions of the CPU described above. The computer system 1201 includes a bus 1202 or other communication mechanism for communicating information, and a processor 1203 coupled with the bus 1202 for processing the information. The computer system 1201 also includes a main memory 1204, such as a random access memory (RAM) or other dynamic storage device (e.g., dynamic RAM (DRAM), static RAM (SRAM), and synchronous DRAM (SDRAM)), coupled to the bus 1202 for storing information and instructions to be executed by processor 1203. In addition, the main memory 1204 may be used for storing temporary variables or other intermediate information during the execution of instructions by the processor 1203. The computer system 1201 further includes a read only memory (ROM) 1205 or other static storage device (e.g., programmable ROM (PROM), erasable PROM (EPROM), and electrically erasable PROM (EEPROM)) coupled to the bus 1202 for storing static information and instructions for the processor 1203.

The computer system 1201 also includes a disk controller 1206 coupled to the bus 1202 to control one or more storage devices for storing information and instructions, such as a magnetic hard disk 1207, and a removable media drive 1208 (e.g., floppy disk drive, read-only compact disc drive, read/write compact disc drive, compact disc jukebox, tape drive, and removable magneto-optical drive). The storage devices may be added to the computer system 1201 using an appropriate device interface (e.g., small computer system interface (SCSI), integrated device electronics (IDE), enhanced-IDE (E-IDE), direct memory access (DMA), or ultra-DMA).

The computer system 1201 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 1201 may also include a display controller 1209 coupled to the bus 1202 to control a display 1210, such as a cathode ray tube (CRT), for displaying information to a computer user. The computer system includes input devices, such as a keyboard 1211 and a pointing device 1212, for interacting with a computer user and providing information to the processor 1203. The pointing device 1212, for example, may be a mouse, a trackball, or a pointing stick for communicating direction information and command selections to the processor 1203 and for controlling cursor movement on the display 1210. In addition, a printer may provide printed listings of data stored and/or generated by the computer system 1201.

The computer system 1201 performs a portion or all of the processing steps of the invention (such as for example those described in relation to FIG. 5) in response to the processor 1203 executing one or more sequences of one or more instructions contained in a memory, such as the main memory 1204. Such instructions may be read into the main memory 1204 from another computer readable medium, such as a hard disk 1207 or a removable media drive 1208. One or more processors in a multi-processing arrangement may also be employed to execute the sequences of instructions contained in main memory 1204. In alternative embodiments, hard-wired circuitry may be used in place of or in combination with software instructions. Thus, embodiments are not limited to any specific combination of hardware circuitry and software.

As stated above, the computer system 1201 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the present invention includes software for controlling the computer system 1201, for driving a device or devices for implementing the invention, and for enabling the computer system 1201 to interact with a human user (e.g., print production personnel). Such software may include, but is not limited to, device drivers, operating systems, development tools, and applications software. Such computer readable media further includes the computer program product of the present invention for performing all or a portion (if processing is distributed) of the processing performed in implementing the invention.

The computer code devices of the present invention may be any interpretable or executable code mechanism, including but not limited to scripts, interpretable programs, dynamic link libraries (DLLs), Java classes, and complete executable programs. Moreover, parts of the processing of the present invention may be distributed for better performance, reliability, and/or cost.

The term "computer readable medium" as used herein refers to any medium that participates in providing instructions to the processor 1203 for execution. A computer readable medium may take many forms, including but not limited to, non-volatile media, volatile media, and transmission media. Non-volatile media includes, for example, optical, magnetic disks, and magneto-optical disks, such as the hard disk 1207 or the removable media drive 1208. Volatile media includes dynamic memory, such as the main memory 1204. Transmission media includes coaxial cables, copper wire and fiber optics, including the wires that make up the bus 1202. Transmission media also may also take the form of acoustic or light waves, such as those generated during radio wave and infrared data communications.

Various forms of computer readable media may be involved in carrying out one or more sequences of one or more instructions to processor 1203 for execution. For example, the instructions may initially be carried on a magnetic disk of a remote computer. The remote computer can load the instructions for implementing all or a portion of the present invention remotely into a dynamic memory and send the instructions over a telephone line using a modem. A modem local to the computer system 1201 may receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1204, from which the processor 1203 retrieves and executes the instructions. The instructions received by the main memory 1204 may optionally be stored on storage device 1207 or 1208 either before or after execution by processor 1203.

The computer system 1201 also includes a communication interface 1213 coupled to the bus 1202. The communication interface 1213 provides a two-way data communication coupling to a network link 1214 that is connected to, for example, a local area network (LAN) 1215, or to another communications network 1216 such as the Internet. For example, the communication interface 1213 may be a network interface card to attach to any packet switched LAN. As another example, the communication interface 1213 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 1213 sends and receives electrical, electromagnetic or optical signals that carry digital data streams representing various types of information.

The network link 1214 typically provides data communication through one or more networks to other data devices. For example, the network link 1214 may provide a connection to another computer through a local network 1215 (e.g., a LAN) or through equipment operated by a service provider, which provides communication services through a communications network 1216. The local network 1214 and the communications network 1216 use, for example, electrical, electromagnetic, or optical signals that carry digital data streams, and the associated physical layer (e.g., CAT 5 cable, coaxial cable, optical fiber, etc). The signals through the various networks and the signals on the network link 1214 and through the communication interface 1213, which carry the digital data to and from the computer system 1201 may be implemented in baseband signals, or carrier wave based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 1201 can transmit and receive data, including program code, through the network(s) 1215 and 1216, the network link 1214, and the communication interface 1213. Moreover, the network link 1214 may provide a connection through a LAN 1215 to a mobile device 1217 such as a personal digital assistant (PDA) laptop computer, or cellular telephone.

The exemplary energy spectrum previously noted in FIG. 1 may also be used in this computer-implemented system.

The reagents and chemicals useful for methods and systems of the present invention may be packaged in kits to facilitate application of the present invention. In one exemplary embodiment, a kit including a psoralen, and fractionating containers for easy fractionation and isolation of autovaccines is contemplated. A further embodiment of kit would comprise at least one activatable pharmaceutical agent capable of causing a predetermined cellular change, at least one energy modulation agent capable of activating the at least one activatable agent when energized, and containers suitable for storing the agents in stable form, and preferably further comprising instructions for administering the at least one activatable pharmaceutical agent and at least one energy modulation agent to a subject, and for applying an initiation energy from an initiation energy source to activate the activatable pharmaceutical agent. The instructions could be in any desired form, including but not limited to, printed on a kit insert, printed on one or more containers, as well as electronically stored instructions provided on an electronic storage medium, such as a computer readable storage medium. Also optionally included is a software package on a computer readable storage medium that permits the user to integrate the information and calculate a control dose, to calculate and control intensity of the irradiation source.

Having generally described this invention, a further understanding can be obtained by reference to certain specific examples which are provided herein for purposes of illustration only and are not intended to be limiting unless otherwise specified.

EXAMPLES

Example 1

In a first example, Vitamin B12 is used as a stimulating energy source for a photoactive agent overlapping its emission wavelength using dipole-dipole resonance energy transfer.

| Endogenous Fluorophore | Excitation Max. (nm) | Emission Max. (nm) |
|---|---|---|
| Vitamin $B_{12}$ | 275 | 305 |

Vitamin B12 has an excitation maximum at about 275 nm and an emission maximum at 305 nm, as shown above and in Table 2. Table 4 shows UV and light emission from gamma ray sources. In this example, $^{113}$Sn and/or $^{137}$Cs are chelated with the Vitamin B12. The Vitamin B12 preferentially is absorbed by tumor cells. Thus, it is in close proximity and capable of activating 8-MOP, which is administered in advance as the photoactivation molecules. The emission band of Vitamin B12 overlaps the excitation band of 8-MOP; therefore, photo and resonance energy transfer occurs, when Vitamin B12 is in close proximity to 8-MOP. 8-MOP is activated and binds to DNA of the tumor cells inducing an auto vaccine effect in vivo.

Example 2

In this example, gold nanoparticles are chelated with the Vitamin B12 complex. A suitable light source is used to stimulate the gold nanoparticles or Vitamin B12 may be chelated with one of the UV emitters listed in Table 4 in addition to the gold nanoparticles. The tumor cells preferentially absorb the Vitamin B12 complexes, such that the activated gold nanoparticles are within 50 nanometers of 8-MOP and/or other photoactivatable molecules previously administered. Therefore, resonance energy transfer activates the photoactivatable molecules, such as 8-MOP, and the activated 8-MOP binds to DNA in tumor cells indusing apoptosis and autovaccine effects.

In a further example, the nanoparticles of gold are clusters of 5 gold atoms encapsulated by poly-amidoamine dendrimers. Thus, the gold nanoparticles emit UV in the correct band for activating 8-MOP and other UV-activatable agents capable of exhibiting photophoresis and/or photodynamic effects.

Cells undergoing rapid proliferation have been shown to have increased uptake of thymidine and methionine. (See, for example, M. E. van Eijkeren et al., Acta Oncologica, 31, 539 (1992); K. Kobota et al., J. Nucl. Med., 32, 2118 (1991) and K. Higashi et al., J. Nucl. Med., 34, 773 (1993)). Since methylcobalamin is directly involved with methionine synthesis and indirectly involved in the synthesis of thymidylate and DNA, it is not surprising that methylcobalamin as well as Cobalt-57-cyanocobalamin have also been shown to have increased uptake in rapidly dividing tissue (for example, see, B. A. Cooper et al., Nature, 191, 393 (1961); H. Flodh, Acta Radiol. Suppl., 284, 55 (1968); L. Bloomquist et al., Experientia, 25, 294 (1969)). Additionally, up regulation in the number of transcobalamin I1 receptors has been demonstrated in several malignant cell lines during their accelerated thymidine incorporation and DNA synthesis (see, J. Lindemans et al., Exp. Cell. Res., 184, 449 (1989); T. Amagasaki et al., Blood, 26, 138 (1990) and J. A. Begly et al., J. Cell Physiol. 156, 43 (1993). Vitamin B12 is water soluble, has no known toxicity, and in excess is excreted by gloinerular filtration. In addition, the uptake of vitamin B12 could potentially be manipulated by the administration of nitrous oxide and other pharmacological agents (D. Swanson et al., Pharmaceuticals in Medical Imaging, MacMillan Pub. Co., NY (1990) at pages 621 628).

A preferred embodiment of the present invention uses a psoralen compound as the activatable pharmaceutical agent (most preferably 8-MOP or AMT), nanoparticles of gold having clusters of 5 gold atoms encapsulated by poly-amidoamine dendrimers as the energy modulation agent, x-rays as the initiation energy source, UV-A as the resultant energy emitted by the energy modulation agent, which upon activation of the psoralen compound results in apoptosis in the target cells.

Obviously, additional modifications and variations of the present invention are possible in light of the above teachings. It is therefore to be understood that within the scope of the appended claims, the invention may be practiced otherwise than as specifically described herein.

The invention claimed is:

1. A method for treating cancer in a subject in need thereof, the method comprising:

administering to the subject a pharmaceutical agent comprising at least one of 8-methoxypsoralen (8-MOP) and 4'-aminomethyl-4,5',8-trimethylpsoralen (AMT) that causes an auto-vaccine effect when activated;

administering to the subject at least one energy modulation agent comprising a phosphorescent, fluorescent, or luminescent agent that, upon reception of an initiation energy, emits light that activates the pharmaceutical agent; and applying the initiation energy from an energy source to the subject, wherein the initiation energy is X-ray energy, wherein the at least one energy modulation agent activates the pharmaceutical agent in situ with said light emitted from the phosphorescent, fluorescent, or luminescent agent, thus causing an auto-vaccine effect, wherein the auto-vaccine effect occurs in vivo in the subject in need, and wherein said auto-vaccine effect treats cancer, and wherein the pharmaceutical agent is activated by one or more sequential single photon absorption events.

2. The method of claim 1, wherein said auto-vaccine effect treats cancer by changing the cell proliferation rate of a cancer cell.

3. The method of claim 1, wherein said at least one energy modulation agent is a single energy modulation agent, and is coupled to said pharmaceutical agent.

4. The method of claim 1, wherein the pharmaceutical agent is contained within a photocage, wherein upon exposure to said X-ray energy, the photocage disassociates from the pharmaceutical agent, rendering the pharmaceutical agent available.

5. The method of claim 1, wherein the pharmaceutical agent is coupled to a carrier that is capable of binding to a receptor site.

6. The method of claim 5, wherein the carrier is one selected from insulin, interleukin, thymopoietin or transferrin.

7. The method of claim 5, wherein the pharmaceutical agent is coupled to the carrier by a covalent bond.

8. The method of claim 5, wherein the pharmaceutical agent is coupled to the carrier by a non-covalent bond.

9. The method of claim 5, wherein the receptor site is one selected from nucleic acids of nucleated cells, antigenic sites on nucleated cells, or epitopes.

10. The method of claim 1, wherein the pharmaceutical agent has affinity for a cancer cell.

11. The method of claim 1, wherein pharmaceutical agent is capable of being preferentially absorbed by a cancer cell.

12. The method of claim 1, wherein the pharmaceutical agent is contained within a photocage and is exposed to light emitted from the phosphorescent, fluorescent, or luminescent agent, wherein upon the exposure to light emitted from the phosphorescent, fluorescent, or luminescent agent, the photocage disassociates from the pharmaceutical agent, rendering the pharmaceutical agent available.

13. The method of claim 1, wherein the at least one energy modulation agent and the pharmaceutical agent are independent and separately movable from each other.

* * * * *

UNITED STATES PATENT AND TRADEMARK OFFICE
CERTIFICATE OF CORRECTION

| | | |
|---|---|---|
| PATENT NO. | : 9,682,146 B2 | Page 1 of 1 |
| APPLICATION NO. | : 14/450756 | |
| DATED | : June 20, 2017 | |
| INVENTOR(S) | : Bourke, Jr. | |

It is certified that error appears in the above-identified patent and that said Letters Patent is hereby corrected as shown below:

On the Title Page

Item (54) and in the Specification, Column 1, Lines 1-3, Title, "METHODS AND SYSTEMS FOR TREATING CELL PROLIFERATION RELATED DISORDERS", should read --METHODS AND SYSTEMS FOR TREATING CELL PROLIFERATION DISORDERS--.

In the Specification

Column 12, Table 1, 1B row, "$1.87 \times 10$", should read --$1.87 \times 10^8$--.

Signed and Sealed this
Eighteenth Day of June, 2019

Andrei Iancu
*Director of the United States Patent and Trademark Office*